US011239928B2

(12) United States Patent
Fishler et al.

(10) Patent No.: US 11,239,928 B2
(45) Date of Patent: Feb. 1, 2022

(54) DYNAMIC SENSITIVITY AND STRENGTH CONTROL OF COMMUNICATION SIGNALS BETWEEN IMPLANTABLE MEDICAL DEVICES

(71) Applicant: Pacesetter, Inc., Sylmar, CA (US)

(72) Inventors: Matthew G. Fishler, Scotts Valley, CA (US); Benjamin T. Persson, Sunnyvale, CA (US); Suresh Gurunathan, Palo Alto, CA (US)

(73) Assignee: Pacesetter, Inc., Sylmar, CA (US)

( * ) Notice: Subject to any disclaimer, the term of this patent is extended or adjusted under 35 U.S.C. 154(b) by 81 days.

(21) Appl. No.: 16/897,014

(22) Filed: Jun. 9, 2020

(65) Prior Publication Data

US 2020/0403717 A1 Dec. 24, 2020

Related U.S. Application Data

(60) Provisional application No. 62/864,753, filed on Jun. 21, 2019.

(51) Int. Cl.
*G01R 31/08* (2020.01)
*G06F 11/00* (2006.01)
(Continued)

(52) U.S. Cl.
CPC ....... *H04B 17/318* (2015.01); *A61N 1/37211* (2013.01); *H04B 1/1638* (2013.01);
(Continued)

(58) Field of Classification Search
CPC .. H04B 17/318; H04B 17/336; H04B 1/1638; H04B 13/005; H04B 7/0608;
(Continued)

(56) References Cited

U.S. PATENT DOCUMENTS 6,427,088 B1 7/2002 Bowman et al.
6,443,891 B1 9/2002 Grevious
(Continued)

FOREIGN PATENT DOCUMENTS

CN 202933393 U 5/2013

OTHER PUBLICATIONS

English Abstract of CN Publication No. CN202933393 published May 15, 2013.

*Primary Examiner* — Stephen M D Agosta
(74) *Attorney, Agent, or Firm* — Vierra Magen Marcus LLP

(57) ABSTRACT

Described herein is an implantable medical device (IMD) that wirelessly communicates another IMD, and methods for use therewith. Such a method can include receiving one or more implant-to-implant (i2i) communication signals from the other IMD using a communication receiver of the IMD, measuring a strength of at least one of the one or more received i2i communication signals or a surrogate thereof, and updating a strength metric based on the measured strength or surrogate thereof. The method further includes determining, based on the updated strength metric, whether to increase, decrease, or maintain the sensitivity of the communication receiver of the IMD, and responding accordingly such that the sensitivity is sometimes increased, sometimes decreased, and sometimes maintained. The method can also include selectively causing a transmitter of the IMD to transmit an i2i communication signal to the other IMD requesting that the other IMD adjust its transmission strength.

20 Claims, 9 Drawing Sheets

(51) Int. Cl.

| | |
|---|---|
| *G08C 15/00* | (2006.01) |
| *H04J 1/16* | (2006.01) |
| *H04J 3/14* | (2006.01) |
| *H04L 1/00* | (2006.01) |
| *H04L 12/26* | (2006.01) |
| *H04B 17/318* | (2015.01) |
| *H04B 1/16* | (2006.01) |
| *H04W 52/24* | (2009.01) |
| *A61N 1/372* | (2006.01) |
| *H04B 17/336* | (2015.01) |
| *A61N 1/362* | (2006.01) |

(52) U.S. Cl.
CPC ........ *H04B 17/336* (2015.01); *H04W 52/245* (2013.01); *A61N 1/362* (2013.01)

(58) Field of Classification Search
CPC .. H04B 7/0814; H04W 52/245; H04W 52/04; H04W 56/001; H04W 4/70; H04W 56/0035; H04W 12/04; H04W 12/06; H04W 12/50; H04W 4/08; H04W 4/12; H04W 4/20; H04W 52/0216; A61N 1/37211; A61N 1/362; A61N 1/3756; A61N 1/37288; A61N 1/37276; A61N 1/37252; A61N 1/37217; A61N 1/37205; H04L 63/0428; H04L 67/12; H04L 1/0061; H04L 1/1812; H04L 1/20; H04L 1/201; H04L 1/24; H04L 2209/42; H04L 2209/80; H04L 9/3271; H02J 50/10; H02J 50/80; H02J 50/90; H02J 7/00034

See application file for complete search history.

(56) References Cited

U.S. PATENT DOCUMENTS

| | | | |
|---|---|---|---|
| 6,522,924 B1 * | 2/2003 | Meier | A61N 1/3712 607/28 |
| 6,535,766 B1 | 3/2003 | Thompson et al. | |
| 6,704,602 B2 | 3/2004 | Berg et al. | |
| 7,218,969 B2 | 5/2007 | Vallapureddy et al. | |
| 7,308,307 B1 * | 12/2007 | Pei | A61N 1/3621 607/17 |
| 7,324,850 B2 * | 1/2008 | Persen | A61N 1/37247 607/30 |
| 7,738,964 B2 | 6/2010 | Von Arx et al. | |
| 7,742,822 B2 | 6/2010 | Masoud et al. | |
| 8,509,911 B2 | 8/2013 | Li et al. | |
| 8,554,333 B2 | 10/2013 | Wu et al. | |
| 8,571,678 B2 | 10/2013 | Wang | |
| 8,607,305 B2 | 12/2013 | Neystadt et al. | |
| 8,744,572 B1 | 6/2014 | Greenhut et al. | |
| 9,168,380 B1 | 10/2015 | Greenhut et al. | |
| 9,764,148 B2 | 9/2017 | Stahmann et al. | |
| 10,052,491 B1 | 8/2018 | Chin | |
| 10,173,068 B2 | 1/2019 | Chin | |
| 10,342,429 B2 | 7/2019 | Chin | |
| 10,632,315 B2 | 4/2020 | Fishler et al. | |
| 2002/0045920 A1 | 4/2002 | Thompson | |
| 2005/0283198 A1 | 12/2005 | Haubrich et al. | |
| 2007/0150028 A1 | 6/2007 | Parkinson et al. | |
| 2008/0027501 A1 | 1/2008 | Haubrich et al. | |
| 2008/0046037 A1 * | 2/2008 | Haubrich | A61B 5/0028 607/60 |
| 2008/0071318 A1 | 3/2008 | Brooke et al. | |
| 2009/0210024 A1 | 8/2009 | Brooke | |
| 2010/0023085 A1 | 1/2010 | Wu et al. | |
| 2011/0082379 A1 | 4/2011 | Sullivan | |
| 2011/0245890 A1 | 10/2011 | Brisben et al. | |
| 2012/0059436 A1 | 3/2012 | Fontaine et al. | |
| 2012/0071098 A1 | 3/2012 | Chebbo et al. | |
| 2012/0277606 A1 | 11/2012 | Ellingson et al. | |
| 2013/0041422 A1 | 2/2013 | Jacobson | |
| 2013/0060298 A1 | 3/2013 | Splett et al. | |
| 2014/0214104 A1 | 7/2014 | Greenhut et al. | |
| 2015/0147073 A1 | 5/2015 | Nonaka | |
| 2016/0038747 A1 | 2/2016 | Maile et al. | |
| 2016/0121127 A1 | 5/2016 | Klimovitch et al. | |
| 2016/0121128 A1 * | 5/2016 | Fishler | A61N 1/37288 607/14 |
| 2016/0121129 A1 | 5/2016 | Persson et al. | |
| 2016/0206892 A1 * | 7/2016 | Demmer | A61N 1/3956 |
| 2016/0250483 A1 | 9/2016 | Klimovitch et al. | |
| 2017/0054516 A1 | 2/2017 | Schmidt et al. | |
| 2017/0132120 A1 | 5/2017 | Salameh et al. | |
| 2017/0216610 A1 | 8/2017 | Yoder et al. | |
| 2017/0246465 A1 * | 8/2017 | Ben-Haim | G16H 20/40 |
| 2017/0257761 A1 | 9/2017 | Rodriguez et al. | |
| 2017/0317518 A1 | 11/2017 | Olson et al. | |
| 2018/0028814 A1 * | 2/2018 | Ghosh | A61N 1/3756 |
| 2018/0178022 A1 * | 6/2018 | Koop | A61N 1/37276 |
| 2018/0207433 A1 | 7/2018 | Koop et al. | |
| 2018/0214703 A1 | 8/2018 | Chin | |
| 2018/0176293 A1 | 11/2018 | Ding et al. | |
| 2020/0086129 A1 * | 3/2020 | Min | A61N 1/37235 |

* cited by examiner

DYNAMIC SENSITIVITY AND STRENGTH CONTROL OF COMMUNICATION SIGNALS BETWEEN IMPLANTABLE MEDICAL DEVICES

PRIORITY CLAIM

This application claims priority to U.S. Provisional Patent Application No. 62/864,753, filed Jun. 21, 2019, which is incorporated herein by reference in its entirety.

FIELD OF TECHNOLOGY

Embodiments described herein generally relate to methods and systems for controlling communication between implantable medical devices (IMDs).

BACKGROUND

The longevity of an implantable medical device (IMD) that is powered by a battery is dependent upon how much power is consumed by electronics of the IMD. Such electronics can be used, e.g., for pacing or delivering other types of stimulation, sensing or otherwise collecting information, as well as for communicating with another device. Accordingly, power may be consumed when pacing or delivering other types of stimulation, collecting information, as well as when communicating with another device. It would be beneficial to reduce power consumption in order to increase the longevity of an IMD.

SUMMARY

Embodiments of the present technology relate to implantable medical devices (IMDs) and methods for use therewith. Certain methods of the present technology are for use by an IMD that wirelessly communicates another IMD. Such a method can include receiving one or more implant-to-implant (i2i) communication signals from the other IMD using a communication receiver of the IMD, measuring a strength of at least one of the one or more received i2i communication signals or a surrogate thereof, and updating a strength metric based on the measured strength or surrogate thereof. The method can further include determining, based on the updated strength metric, whether to increase, decrease, or maintain the sensitivity of the communication receiver of the IMD. The method can further include increasing, decreasing, or maintaining the sensitivity of the communication receiver of the IMD, based on a result of the determining, in a manner that respectively increases, decreases, or maintains an energy usage level of the communication receiver. Such steps are repeated from time-to-time such that sometimes the sensitivity is increased, sometimes the sensitivity is decreased, and sometimes the sensitivity is maintained.

In accordance with certain embodiments, the updated strength metric is compared to one or more thresholds, and determining whether to increase, decrease, or maintain the sensitivity of the communication receiver of the IMD is based on results of the comparisons to the threshold(s). In accordance with certain embodiments, a method includes monitoring at least one of an activity level or a surrogate thereof of the patient, and adjusting (based on the activity level of the patient or the surrogate thereof) at least one of the one or more thresholds to which the updated strength metric is/are compared.

In accordance with certain embodiments, when the result of the determining (whether to increase, decrease, or maintain the sensitivity of the communication receiver of the IMD) is that the sensitivity of the communication receiver of the IMD is to be increased, the increasing the sensitivity of the communication receiver of the IMD, in a manner that increases the energy usage level of the communication receiver of the IMD, comprises increasing at least one of a gain, a bias current, or a switching frequency of an amplifier of the communication receiver of the IMD. Conversely, when the result of the determining (whether to increase, decrease, or maintain the sensitivity of the communication receiver of the IMD) is that the sensitivity of the communication receiver of the IMD is to be decreased, the decreasing the sensitivity of the communication receiver of the IMD, in a manner that decreases the energy usage level of the communication receiver of the IMD, comprises decreasing at least one of a gain, a bias current, or a switching frequency of an amplifier of the communication receiver of the IMD.

In accordance with certain embodiments, the strength of at least one of the one or more received i2i communication signals or the surrogate thereof (that is measured and used to update the strength metric) is indicative of at least one of the following: a measure of amplitude of at least a portion of at least one of the one or more received i2i communication signals; a magnitude of at least a portion of at least one of the one or more received i2i communication signals after rectification and integration thereof; a signal-to-noise ratio (SNR) of at least a portion of at least one of the one or more received i2i communication signals; a total energy of at least a portion of at least one of the one or more received i2i communication signals; or a bit-error-rate (BER) associated with at least a portion of at least one of the one or more received i2i communication signals.

In accordance with certain embodiments, the strength metric can be updated based on the measured strength or surrogate thereof by replacing a previous value of the strength metric with the measured strength or surrogate thereof, or by updating a moving average value of the strength metric using the measured strength or surrogate thereof, but is not limited thereto.

In accordance with certain embodiments, the sensitivity of the communication receiver of the IMD is adjustable within a sensitivity range that includes a minimum sensitivity setting and a maximum sensitivity setting. In certain such embodiments, when the communication receiver is already at the maximum sensitivity setting and the result of the determining is that the sensitivity of the communication receiver is to be increased, the IMD transmits an i2i communication signal to the other IMD that requests that the other IMD increase a strength of one or more future i2i communication signals that will be transmitted by the other IMD to the IMD. Further, when the communication receiver is already at the minimum sensitivity setting and the result of the determining is that the sensitivity of the communication receiver is to be decreased, the IMD transmits an i2i communication signal to the other IMD that requests that the other IMD decrease a strength of one or more future i2i communication signals that will be transmitted by the other IMD to the IMD.

In accordance with certain embodiments, the communication receiver of the IMD has a minimum acceptable SNR associated with the communication receiver of the IMD. At any given time there is a combination of a level of the sensitivity of the communication receiver that receives i2i communication signals from the other IMD, and a level of transmitter strength associated with the other IMD from which the IMD receives i2i communication signals. In accordance with certain embodiments, determining, based on the updated strength metric, whether to increase, decrease, or maintain the sensitivity of the communication receiver of the IMD comprises determining whether there is another combination of the level of the sensitivity of the communication receiver of the IMD that receives i2i communication signals from the other IMD, and the level of transmitter strength associated with the other IMD from which the IMD receives i2i communication signals, that will reduce a total system energy usage while satisfying the minimum acceptable SNR associated with the communication receiver. In such an embodiment, in response to determining that there is another combination that will reduce the total system energy usage while satisfying the minimum acceptable SNR, a method involves modifying the sensitivity of the communication receiver and/or transmitting an i2i communication signal to the other IMD that requests that the other IMD modify the strength of one or more future i2i communication signals, in order to implement the other combination and thereby reduce the total system energy usage while still satisfying the minimum acceptable SNR.

In accordance with certain embodiments, a method further includes detecting when it is likely that the other IMD transmitted an i2i communication signal that was not received by the communication receiver of the IMD, and in response to detecting that it is likely that the other IMD transmitted an i2i communication signal that was not received by the communication receiver of the IMD, increasing the sensitivity of the communication receiver of the IMD. Alternatively, or additionally, a method can include transmitting an i2i communication signal to the other IMD that requests that the other IMD modify the strength of one or more future i2i communication signals that will be transmitted by the other IMD to the IMD, in response to detecting that it is likely that the other IMD transmitted an i2i communication signal that was not received by the communication receiver of the IMD. The term "likely" as used herein, when referring to a condition or event as likely to be present or to have occurred, means there is at least a 50% probability of that the condition or event is present or has occurred.

In accordance with certain embodiments, the i2i communication signals that the communication receiver of the IMD receives from the other IMD comprise both primary i2i communication signals and secondary i2i communication signals, wherein the primary i2i communication signals are for use in controlling delivery of therapy, and wherein the secondary i2i communication signals are for using in controlling the sensitivity of the communication receiver of the IMD. In certain such embodiments, the measuring the strength of at least one of the one or more received i2i communication signals or a surrogate thereof, comprises measuring the strength of at least one of the secondary i2i communications signals.

In accordance with certain embodiments, the measuring the strength of at least one of the one or more received i2i communication signals or a surrogate thereof, and the updating the strength metric, takes into account where within individual cardiac cycles different ones of the i2i communication signals are received. In certain such embodiments, a method can also include determining that an adjustment to when the other IMD transmits i2i communication signals within cardiac cycles enables the IMD to reduce the sensitivity and energy usage of the communication receiver of the IMD. The method can further include transmitting an i2i communication signal to the other IMD requesting that the other IMD adjust when the other IMD transmits i2i communication signals within individual cardiac cycles to thereby enable the IMD to reduce the sensitivity and energy usage of the communication receiver of the IMD.

Certain embodiments of the present technology are directed to an IMD capable of wirelessly communicating with another IMD implanted within a patient, where the IMD includes a communication receiver, measurement circuitry, a controller, and a battery (that powers the communication receiver, the measurement circuitry, and the controller). The communication receiver is configured to receive i2i communication signals from the other IMD. The measurement circuitry is configured to measure a strength, or surrogate thereof, of one or more i2i communication signals received by the communication receiver from the other IMD. The controller, which is communicatively coupled to the communication receiver and the measurement circuitry, is configured to update a strength metric based on the measured strength (or surrogate thereof) of one or more i2i communication signals received by the communication receiver, as measured by the measurement circuitry. The controller is further configured to selectively increase, decrease, or maintain the sensitivity of the communication receiver of the IMD, based on the updated strength metric, in a manner that respectively increases, decreases, or maintains a level of energy that the communication receiver uses from the battery.

In accordance with certain embodiments, the IMD further includes a communication transmitter configured to transmit i2i communication signals to the other IMD. In certain such embodiments, the controller is configured to selectively cause the transmitter to transmit an i2i communication signal to the other IMD that requests that the other IMD adjust a strength of one or more future i2i communication signals that will be transmitted by the other IMD to the IMD.

In accordance with certain embodiments, the sensitivity of the communication receiver is adjustable within a sensitivity range that includes a minimum sensitivity setting and a maximum sensitivity setting. In certain such embodiments, the controller is configured to compare the updated strength metric to one or more thresholds to make a determination as to whether the sensitivity of the communication receiver is to be increased, decreased or maintained. Further, the controller can be configured to cause the transmitter to transmit an i2i communication signal to the other IMD that requests that the other IMD increase a strength of one or more future i2i communication signals that will be transmitted by the other IMD to the IMD, when the communication receiver of the IMD is already at the maximum sensitivity setting and the determination is that the sensitivity of the communication receiver of the IMD is to be increased. Additionally, the controller can be configured to cause the transmitter to transmit an i2i communication signal to the other IMD that requests that the other IMD decrease a strength of one or more future i2i communication signals that will be transmitted by the other IMD to the IMD, when the communication receiver of the IMD is already at the minimum sensitivity setting and the determination is that the sensitivity of the communication receiver of the IMD is to be decreased.

In accordance with certain embodiments, the controller is further configured to detect when it is likely that the other IMD transmitted an i2i communication signal that was not received by the communication receiver of the IMD, and configured to cause the transmitter to transmit an i2i communication signal to the other IMD that requests that the other IMD increase the strength of one or more future i2i communication signals that will be transmitted by the other IMD to the IMD, in response to detecting that it is likely that the other IMD transmitted an i2i communication signal that was not received by the communication receiver of the IMD. Alternatively, or additionally, the controller can be configured to increase the sensitivity of the communication receiver of the IMD, in response to detecting that it is likely that the other IMD transmitted an i2i communication signal that was not received by the communication receiver of the IMD.

In accordance with certain embodiments, the IMD also includes a sensor communicatively coupled to the controller, and the controller is further configured to determine whether to increase, decrease, or maintain the sensitivity of the communication receiver of the IMD based on comparisons between the updated strength metric and one or more thresholds. In such an embodiment, the controller can be configured to use the sensor to monitor at least one of an activity level or a surrogate thereof of a patient within which the IMD is implanted, and adjust at least one of the one or more thresholds based on the activity level of the patient or the surrogate thereof that is monitored using the sensor.

Certain embodiments of the present technology are directed to an implantable system, comprising first and second IMDs (e.g., leadless pacemakers) capable of wirelessly communicating with one another via i2i communication signals. In such embodiments, the first and second IMDs each including a respective communication receiver, a respective transmitter, respective controller, and a respective battery. The controller of the first IMD is configured to dynamically control a sensitivity of the communication receiver of the first IMD based on measures indicative of strength of i2i communication signals received from the second IMD. The controller of the second IMD is configured to dynamically control a sensitivity of the communication receiver of the second IMD based on measures indicative of strength of i2i communication signals received from the first IMD. In accordance with certain such embodiments, the controller of the first IMD is configured to cause the transmitter of the first IMD to selectively transmit an i2i communication signal to the second IMD that requests that the second IMD adjust a strength of one or more future i2i communication signals that will be transmitted by the second IMD to the first IMD. Additionally, the controller of the second IMD is configured to cause the transmitter of the second IMD to selectively transmit an i2i communication signal to the first IMD that requests that the first IMD adjust a strength of one or more future i2i communication signals that will be transmitted by the first IMD to the second IMD. In certain such embodiments, the first IMD comprises a first leadless pacemaker configured to be implanted in or on a first cardiac chamber, and the second IMD comprises a second leadless pacemaker configured to be implanted in or on a second cardiac chamber that differs from the first cardiac chamber.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Figure 1A:
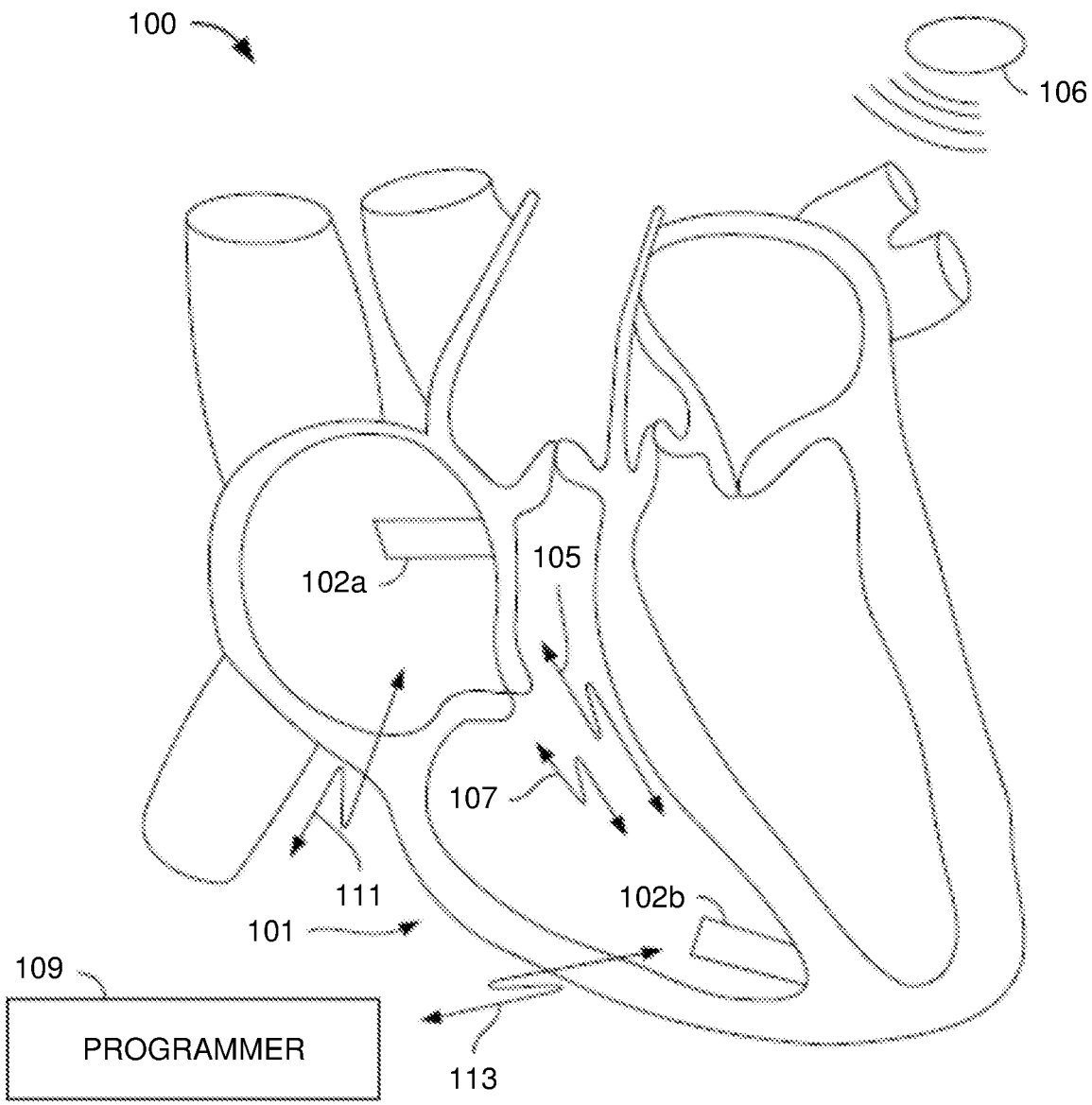
FIG. 1A illustrates a system formed in accordance with certain embodiments herein as implanted in a heart.

Conventionally, implantable medical devices (IMDs) that had wireless communication capabilities used their communication capabilities to communicate with external devices, such as, but not limited, clinical programmers, bedside monitors, and/or the like. More recently, implantable systems have been proposed wherein such implantable systems include multiple (i.e., two or more) IMDs that are intended to communicate with one another. An example of such a proposed implantable system is one including multiple leadless pacemaker (LPs). Such an implantable leadless pacemaker system can include, for example, a first LP implanted in the right atrial (RA) chamber and a second LP implanted in the right ventricular (RV) chamber. In such an implantable system, in order to provide coordinated pacing in multiple cardiac chambers, e.g., the RA and RV chambers, the LPs implanted in those chambers should be capable of communicating with one another. Such communication between multiple IMDs, which can be referred to as implant-to-implant (i2i) communication, consumes power, and thus, can reduce the longevity of the IMDs.

Embodiments of the present technology provide for dynamic control of wireless communication between IMDs, such as, but not limited to, between LPs. Unless stated otherwise, all communication between IMDs discussed herein are assumed to be wireless communication. Accordingly, for brevity, such wireless communication is often referred to herein more succinctly as communication, or as i2i communication.

Communication between IMDs, such as LPs, can be used to coordinate and synchronize functionality between those IMDs. In some cases, such communication may be unidirectional, while in other cases the communication may be bidirectional, or even multi-directional (e.g., one-to-multiple, etc.). Furthermore, in some cases, such communication may be used occasionally or infrequently, while in other cases such communication may be used quite regularly (e.g., every cardiac cycle for certain LPs). In all cases, such communication involves one IMD transmitting a signal and another IMD receiving that signal. The success of each communication requires that the transmission be of sufficient strength (e.g., amplitude) such that the receiving IMD can receive that communication with sufficient signal-to-noise (SNR) fidelity, wherein the SNR can depend on various factors, such as noise in a communication channel, the positions of the IMDs relative to one another (which may change with changes in posture, and/or throughout a cardiac cycle, etc.), a sensitivity of a communication receiver, and/or a strength of a communication signal transmitted by a communication transmitter. Under relatively static conditions, it might be sufficient to program the IMDs with a specific combination of transmitter strength and receiver sensitivity such that those settings remain adequate chronically even after the patient leaves a programming session. However, under more dynamic conditions in which the SNR might be expected to vary over time after the patient leaves the programming session (e.g., due to changes in battery level, and/or as influenced by patient posture, activities, etc., throughout each day), another approach would be to program the IMDs with a specific static combination of transmitter strength and receiver sensitivity that also includes additional static safety factor sufficient to cover that anticipated SNR variability. However, the additional static safety factor has two main short-comings. First, while the selected safety factor provides additional robustness against loss of communication, it may still be insufficient if the SNR falls below the receiving IMD's minimum sensitivity level despite that additional safety factor. The mitigator against this risk is to program the highest safety factor possible. Second, the additional safety factor typically costs additional energy from one or more of the IMDs, with that energy cost typically proportional to the magnitude of the additional safety factor. The additional energy to support the selected safety factor will correspondingly shorten the longevity of those IMDs. The mitigator against this cost is to program the lowest safety factor possible. Thus, under the above scenario, a clinician must make a robustness-versus-longevity tradeoff decision with incomplete information when programming the IMDs.

Certain embodiments of the present technology dynamically adjust receiver sensitivity and/or transmission strength from time-to-time, e.g., on a periodic basis based on the strength of one or more previously received i2i communication signals. In certain such embodiments, such dynamic adjustment can occur as frequently as a beat-by-beat basis (or potentially even more often), but can alternatively occur less frequently, depending upon the specific implementation. In this way, the safety factor employed by these IMDs is dynamically managed and adjusted directly by the IMDs in real-time (instead of by a clinician at the time of programming the IMD) to efficiently meet the needed SNR for successful communications in such a way that modifies (and preferably optimizes) the safety factor over time and thus also reduces (and preferably minimizes) energy usage and increases (and preferably maximizes) IMD longevity.

Before providing addition details of the specific embodiments of the present technology mentioned above, an exemplary system in which embodiments of the present technology can be used will first be described with reference to FIG. 1A through FIG. 5 (aka FIGS. 1A-5). More specifically, FIGS. 1A-5 will be used to describe an exemplary cardiac pacing system, wherein pacing and sensing operations can be performed by multiple medical devices, which may include one or more LPs, an ICD, such as a subcutaneous-ICD, and/or a programmer to reliably and safely coordinate therapeutic and/or diagnostic (e.g., pacing and/or sensing) operations.

FIG. 1 illustrates a system 100 that is configured to be implanted in a heart 101. The system 100 includes two or more leadless pacemakers (LPs) 102a and 102b located in different chambers of the heart. LP 102a is located in a right atrium, while LP 102b is located in a right ventricle. LPs 102a and 102b communicate with one another to inform one another of various local physiologic activities, such as local intrinsic events, local paced events and the like. LPs 102a and 102b may be constructed in a similar manner, but operate differently based upon which chamber LP 102a or 102b is located. The LPs 102a and 102b may sometimes be referred to collectively herein as the LPs 102, or individually as an LP 102.

In certain embodiments, LPs 102a and 102b communicate with one another, and/or with an ICD 106, by conductive communication through the same electrodes that are used for sensing and/or delivery of pacing therapy. The LPs 102a and 102b may also be able to use conductive communications to communicate with an external device, e.g., a programmer 109, having electrodes placed on the skin of a patient within which the LPs 102a and 102b are implanted. While not shown (and not preferred, since it would increase the size and power consumption of the LPs 102a and 102b), the LPs 102a and 102b can potentially include an antenna and/or telemetry coil that would enable them to communicate with one another, the ICD 106 and/or an external device using RF or inductive communication. While only two LPs are shown in FIG. 1A, it is possible that more than two LPs can be implanted in a patient. For example, to provide for bi-ventricular pacing and/or cardiac resynchronization therapy (CRT), in addition to having LPs implanted in or on the right atrial (RA) chamber and the right ventricular (RV) chamber, a further LP can be implanted in or on the left ventricular (LV) chamber.

In some embodiments, one or more LPs 102 can be co-implanted with the ICD 106. Each LP 102 uses two or more electrodes located within, on, or within a few centimeters of the housing of the pacemaker, for pacing and sensing at the cardiac chamber, for bidirectional communication with one another, with the programmer 109, and the ICD 106.

While the methods, devices and systems described herein include examples primarily in the context of LPs, it is understood that the methods, devices and systems described herein may be utilized with various other types of IMDs. By way of example, the methods, devices and systems may dynamically control communication between various IMDs implanted in a human, not just LPs. Certain embodiments enable a first IMD to receive communications from at least a second IMD through conductive communication over at least a first channel. It should also be understood that the embodiments described herein can be used for communication between more than two IMDs, and are not limited to communication between just first and second IMDs. The methods, devices and systems may also be used for communication between two or more IMDs implanted within the same chamber that may be the same type of IMD or may be different types of IMDs. The methods, devices and systems may also be used for communication between two or more IMDs in a system including at least one IMD that is not implanted within a cardiac chamber, but rather, is implanted epicardially, transmurally, intravascularly (e.g., coronary sinus), or subcutaneously (e.g., S-ICD), etc.

Figure 1B:
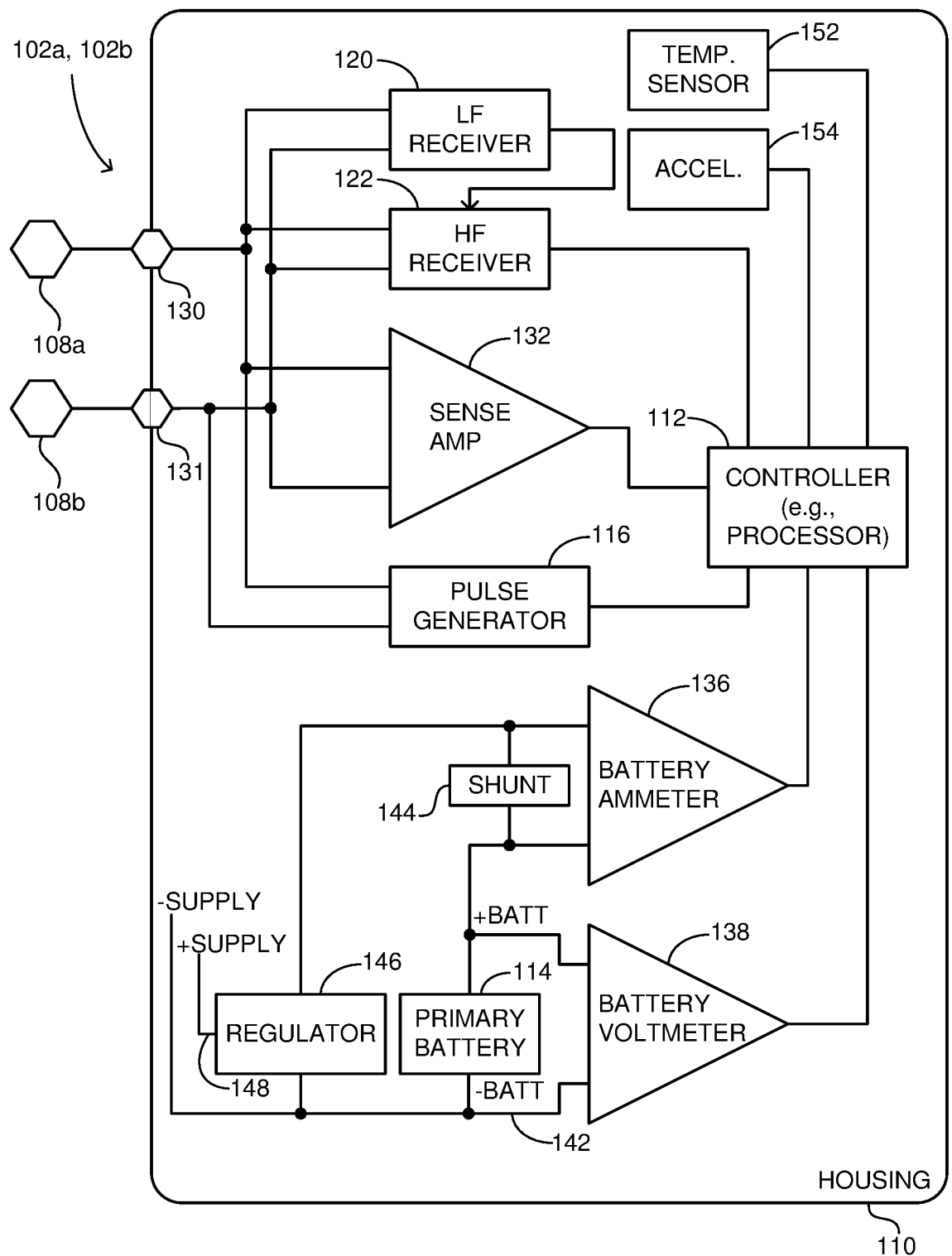
FIG. 1B is a block diagram of a single leadless pacemaker (LP) in accordance with certain embodiments herein.

Referring to FIG. 1B, a block diagram shows an embodiment for portions of the electronics within LPs 102a, 102b configured to provide conductive communication through the sensing/pacing electrode. One or more of LPs 102a and 102b include at least two leadless electrodes configured for delivering cardiac pacing pulses, sensing evoked and/or natural cardiac electrical signals, and uni-directional or bi-directional communication. In FIG. 1B (and FIG. 2) the two electrodes shown therein are labeled 108a and 108b. Such electrodes can be referred to collectively as the electrodes 108, or individually as an electrode 108. An LP 102, or other type of IMD, can include more than two electrodes 108, depending upon implementation.

In FIG. 1B, each of the LPs 102a, 102b is shown as including first and second receivers 120 and 122 that collectively define separate first and second communication channels 105 and 107 (FIG. 1A), (among other things) between LPs 102a and 102b. Although first and second receivers 120 and 122 are depicted, in other embodiments, each LP 102a, 102b may only include the first receiver 120, or may include additional receivers other than first and second receivers 120 and 122. As will be described in additional detail below, the pulse generator 116 can function as a transmitter that transmits i2i communication signals using the electrodes 108. In certain embodiments, LPs 102a and 102b may communicate over more than just first and second communication channels 105 and 107. In certain embodiments, LPs 102a and 102b may communicate over one common communication channel 105. More specifically, LPs 102a and 102b can communicate conductively over a common physical channel via the same electrodes 108 that are also used to deliver pacing pulses. Usage of the electrodes 108 for communication enables the one or more LPs 102a and 102b to perform antenna-less and telemetry coil-less communication.

The receivers 120 and 122 can also be referred to, respectively, as a low frequency (LF) receiver 120 and a high frequency (HF) receiver 122, because the receiver 120 is configured to monitor for one or more signals within a relatively low frequency range (e.g., below 200 kHz) and the receiver 122 is configured to monitor for one or more signals within a relatively high frequency range (e.g., above 200 kHz). In certain embodiments, the receiver 120 (and more specifically, at least a portion thereof) is always enabled and monitoring for a wakeup notice, which can simply be a wakeup pulse, within a specific low frequency range (e.g., between 20 kHz and 200 kHz); and the receiver 122 is selectively enabled by the receiver 120. The receiver 120 is configured to consume less power than the receiver 122 when both the first and second receivers are enabled. Accordingly, the receiver 120 can also be referred to as a low power receiver 120, and the receiver 122 can also be referred to as a high power receiver 122. The low power receiver 120 is incapable of receiving signals within the relatively high frequency range (e.g., above 200 kHz), but consumes significantly less power than the high power receiver 122. This way the low power receiver 120 is capable of always monitoring for a wakeup notice without significantly depleting the battery (e.g., 114) of the LP. In accordance with certain embodiments, the high power receiver 122 is selectively enabled by the low power receiver 120, in response to the low power receiver 120 receiving a wakeup notice, so that the high power receiver 122 can receive the higher frequency signals, and thereby handle higher data throughput needed for effective i2i communications without unnecessarily and rapidly depleting the battery of the LP (which the high power receiver 122 may do if it were always enabled).

In accordance with certain embodiments, when one of the LPs 102a and 102b senses an intrinsic event or delivers a paced event, the corresponding LP 102a, 102b transmits an implant event message to the other LP 102a, 102b. For example, when an atrial LP 102a senses/paces an atrial event, the atrial LP 102a transmits an implant event message including an event marker indicative of a nature of the event (e.g., intrinsic/sensed atrial event, paced atrial event). When a ventricular LP 102b senses/paces a ventricular event, the ventricular LP 102b transmits an implant event message including an event marker indicative of a nature of the event (e.g., intrinsic/sensed ventricular event, paced ventricular event). In certain embodiments, each LP 102a, 102b transmits an implant event message to the other LP 102a, 102b preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice, wakeup pulse or wakeup signal) followed by an event marker. The notice trigger pulse (also referred to as the wakeup notice, wakeup pulse or wakeup signal) is transmitted over a first channel (e.g., with a pulse duration of approximately 5 µs to approximately 50 µs and/or within a fundamental frequency range of approximately 20 kHz to approximately 200 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any i2i communication signal from another LP (or other IMD) or from an external device may transmit a receive acknowledgement indicating that the receiving LP (or other IMD) received the i2i communication signal. In certain embodiments, where an IMD expects to receive an i2i communication signal within a window, and fails to receive the i2i communication signal within the window, the IMD may transmit a failure-to-receive acknowledgement indicating that the receiving IMD failed to receive the i2i communication signal. Other variations are also possible and within the scope of the embodiments described herein.

The event messages enable the LPs 102a, 102b to deliver synchronized therapy and additional supportive features (e.g., measurements, etc.). To maintain synchronous therapy, each of the LPs 102a and 102b is made aware (through the event messages) when an event occurs in the chamber containing the other LP 102a, 102b. Some embodiments described herein provide efficient and reliable processes to maintain synchronization between LPs 102a and 102b without maintaining continuous communication between LPs 102a and 102b. In accordance with certain embodiments herein, low power event messages/signaling may be maintained between LPs 102a and 102b synchronously or asynchronously.

For synchronous event signaling, LPs 102a and 102b maintain synchronization and regularly communicate at a specific interval. Synchronous event signaling allows the transmitter and receivers in each LP 102,102b to use limited (or minimal) power as each LP 102a, 102b is only powered for a small fraction of the time in connection with transmission and reception. For example, LP 102a, 102b may transmit/receive (Tx/Rx) communications in time slots, where the Tx/Rx time slots occur periodically.

LPs 102a and 102b may lose synchronization, even in a synchronous event signaling scheme. As explained herein, features may be included in LPs 102a and 102b to maintain device synchronization, and when synchronization is lost, LPs 102a and 102b undergo operations to recover synchronization. Also, synchronous event messages/signaling may introduce a delay between transmissions which causes a reaction lag at the receiving LP 102a, 102b. Accordingly, features may be implemented to account for the reaction lag.

During asynchronous event signaling, LPs 102a and 102b do not maintain communication synchronization. During asynchronous event signaling, one or more of receivers 120 and 122 of LPs 102a and 102b may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of 1/500 to 1/10000. A gain factor may be 1/1000th. Transmit current is a design factor in addition to receiver current. As an example, the system may allocate one-half of the implant communication current budget to the transmitter (e.g., 0.5 µA for each transmitter). When LP 102a, 102b maintains a transmitter in a continuous on-state and the electrode load is 500 ohms, a transmitted voltage may be 2.5V. When an event signal is transmitted at 2.5V, the event signal is attenuated as it propagates and would appear at LP 102a, 102b receiver as an amplitude of approximately 0.25 mV.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

In accordance with certain embodiments herein, LPs 102a and 102b may utilize multi-stage receivers that implement a staged receiver wakeup scheme in order to improve reliability yet remain power efficient. Each of LPs 102a and 102b may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., from 20 kHz to 200 kHz) as compared to the fundamental frequency range (e.g., greater than 200 kHz) assigned to the second receive channel.

In accordance with certain embodiments, the first receiver 120 may maintain the first channel active (awake) at all times (including when the second channel is inactive (asleep)) in order to listen for messages from a remote LP. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP). The terms active, awake and enabled are used interchangeably herein.

Still referring to FIG. 1B, each LP 102a, 102b is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial-to-atrial escape interval (AAEI), ventricular-to-ventricular escape interval (VVEI) etc.). Such timing control circuitry may also be used for the timing of refractory periods, other escape intervals, other delays, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102a, 102b is located, such as when the associated chamber is not in a refractory state. In addition, a LP 102a, 102b that receives an event message may enter an "event refractory" state (or event blanking state) following receipt of the event message. The event refractory/blanking state may be set to extend for a determined period of time after receipt of an event message in order to avoid the receiving LP 102a, 102b from inadvertently sensing another signal as an event message that might otherwise cause retriggering. For example, the receiving LP 102a, 102b may detect a measurement pulse from another LP 102a, 102b or programmer 109.

In accordance with certain embodiments herein, programmer 109 may communicate over a programmer-to-LP channel, with LP 102a, 102b utilizing the same communication scheme. The external programmer may listen to the event message transmitted between LP 102a, 102b and synchronize programmer to implant communication such that programmer 109 does not transmit communication signals 113 until after an implant to implant messaging sequence is completed.

In accordance with certain embodiments, LP 102a, 102b may combine transmit operations with therapy. The transmit event marker may be configured to have similar characteristics in amplitude and pulse-width to a pacing pulse and LP 102a, 102b may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102a, 102b may implement an event message utilizing event signaling parameters for amplitude, pulse-width, pulse rate, etc. that correspond to a current draw of approximately 0.5 µA for transmit.

LP 102*a*, 102*b* may combine the event message transmissions with pacing pulses. For example, LP 102*a*, 102*b* may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102*a* or 102*b* senses an intrinsic event, it can send a qualitatively similar event pulse sequence (but indicative of a sensed event) without adding the pace pulse remainder. As LP 102*a*, 102*b* longevity calculations are designed based on the assumption that LP 102*a*, 102*b* will deliver pacing therapy 100% of the time, transmitting an intrinsic event marker to another LP 102*a*, 102*b* will not impact the nominal calculated LP longevity.

In some embodiments, LP 102*a*, 102*b* may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102*a*, 102*b* increases an extent to which LP 102*a*, 102*b* uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102*a*, 102*b* may use larger pulse-widths.

By combining event messages and low power pacing, LP 102*a*, 102*b* may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

While not shown, a communication capacitor can be provided in LP 102*a*, 102*b*. The communication capacitor may be used to transmit event signals having higher voltage for the event message pulses to improve communication, such as when the LPs 102*a* and 102*b* experience difficulty sensing event messages. The high voltage event signaling may be used for implants with high signal attenuation or in the case of a retry for an ARQ (automatic repeat request) handshaking scheme.

In some embodiments, the individual LP 102*a* can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 1B depicts a single LP 102*a* (or 102*b*) and shows the LP's functional elements substantially enclosed in a hermetic housing 110. The LP 102*a* (or 102*b*) has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102*a*, 102*b* that receives the event message reacts as directed by the event message depending on the message origin or location. In some embodiments or conditions, the two or more leadless electrodes 108 can be configured to communicate bidirectionally among the one or more leadless cardiac pacemakers 102*a* and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102*a*, 102*b* can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 102*b* may receive and relay an event message from LP 102*a* to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1A and 1B, the cardiac pacing system 100 may comprise an ICD 106 in addition to one or more LPs 102*a*, 102*b* configured for implantation in electrical contact with a cardiac chamber and for performing cardiac rhythm management functions in combination with the implantable ICD 106. The implantable ICD 106 and the one or more LPs 102*a*, 102*b* configured for leadless intercommunication by information conduction through body tissue and/or wireless transmission between transmitters and receivers in accordance with the discussed herein.

In a further embodiment, a cardiac pacing system 100 comprises at least one LP 102*a*, 102*b* configured for implantation in electrical contact with a cardiac chamber and configured to perform cardiac pacing functions in combination with the co-implanted ICD 106. The leadless cardiac pacemaker or pacemakers 102*a* comprise at least two leadless electrodes 108 configured for delivering cardiac pacing pulses, sensing evoked and/or natural cardiac electrical signals, and transmitting information to the co-implanted ICD 106.

As shown in the illustrative embodiments, a leadless cardiac pacemaker 102*a*, 102*b* can comprise two or more leadless electrodes 108 configured for delivering cardiac pacing pulses, sensing evoked and/or natural cardiac electrical signals, and bidirectionally communicating with the co-implanted ICD 106.

LP 102*a*, 102*b* can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102*a*, 102*b* receiving the communication decode the information and respond depending on location of the receiving pacemaker and predetermined system functionality.

In some embodiments, the LPs 102*a* and 102*b* are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or WI), and for the IPG to utilize the proper set of settings and algorithms (e.g., V-AutoCapture vs ACap-Confirm, sensing sensitivities, etc.).

Also shown in FIG. 1B, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114.

Referring to FIG. 1B, the LP is shown as including a temperature sensor 152. The temperature sensor can be any one of various different types of well-known temperature sensors, or can be a future developed temperature sensor. For one example, the temperature sensor 152 can be a thermistor, a thermocouple, a resistance thermometer, or a silicon bandgap temperature sensor, but is not limited thereto. Regardless of how the temperature sensor 152 is implemented, it is preferably that the temperature sensed by the sensor is provided to the controller 112 as a digital signal indicative of the blood temperature of the patient within which the LP is implanted. The temperature sensor 152 can be hermetically sealed within the housing 110, but that need not be the case. The temperature sensor 152 can be used in various manners. For example, the temperature sensor 152 can be used to detect an activity level of the patient to adjust a pacing rate, i.e., for use in rate responsive pacing. When a person starts to exercise their core body temperature initially dips, and then after exercising for a prolonged period of time the person's core body temperature will eventually rise. Thereafter, when the person stops exercising their core body temperature will return to its baseline. Accordingly, the controller 112 can be configured to detect an activity level of a patient based on core blood temperature measurements obtained using the temperature sensor 152.

Referring to FIG. 1B, the LP is also shown as including an accelerometer 154 which can be hermetically contained within the housing 110. The accelerometer 154 can be any one of various different types of well-known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. For example, the accelerometer 154 can be used to detect an activity level of the patient to adjust a pacing rate, i.e., for use in rate responsive pacing. It would also be possible to use outputs of both the accelerometer 154 and the temperature sensor 152 to monitor the activity level of a patient. Alternatively, or additionally, a patient's activity level can be monitored based on their heart rate, as detected from an IEGM sensed using the electrodes 108, and/or sensed using a plethysmography signal obtained using a plethysmography sensor (not shown) or a heart sound sensor (not shown), but not limited thereto.

The accelerometer 154 can be, e.g., a one-dimensional (1D) accelerometer (also known as a one-axis accelerometer), a two-dimensional (2D) accelerometer (also known as a two-axis accelerometer), or a three-dimensional (3D) accelerometer (also known as a three-axis accelerometer). A 1D accelerometer measures acceleration along one axis, e.g., the z-axis. A 2D accelerometer measures acceleration along two axes that are orthogonal to one another, e.g., the z-axis, and the x- or y-axis. A 3D accelerometer measures acceleration along three axes that are orthogonal to one another, e.g., the z-axis, the x-axis, and the y-axis. Each measure of acceleration (i.e., rate of change of velocity) can actually be a measure of proper acceleration, which is the rate of change of velocity of a body in its own instantaneous rest frame. For example, an accelerometer at rest on the surface of the Earth will measure an acceleration due to Earth's gravity, straight upwards (by definition) of g$\approx$9.81 m/s$^2$.

Where an LP includes an accelerometer within a housing of the LP or attached thereto, the accelerometer can be used to measure the acceleration of the LP along one or more axes, which measurement(s) can be used to determine the orientation of the LP. Accordingly, because the output(s) of the accelerometer can be used to determine the orientation of the LP, it can be said that the output(s) of the accelerometer (e.g., 154) are indicative of an orientation of the LP (e.g., LP 102 or 104). More specifically, in accordance with certain embodiments, the controller 112 of an LP 102 (or 104) receives one or more outputs output(s) of the accelerometer 154, which is/are indicative of an orientation of the LP 102 (or 104). In such embodiments, the controller 112 can determine, based on the output(s) received from the accelerometer 154, an actual orientation of the LP 102 (or 104). Each output of the accelerometer 154 can comprise a respective signal.

One or more signals produced and output by the accelerometer 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 154 can be analog signals, which can be analyzed in the analog domain, or can be converted to digital signals (by an analog-to-digital converter) and analyzed in the digital domain. Alternatively, the signals output by the accelerometer 154 can already be in the digital domain.

The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology. In accordance with certain embodiments of the present technology, described in additional detail below, a sensor signal produced by the accelerometer 154 of an LP implanted in or on a cardiac chamber can be used to detect mechanical cardiac activity associated with another cardiac chamber.

In various embodiments, LP 102a, 102b can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one leadless cardiac pacemaker 102a can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 2:
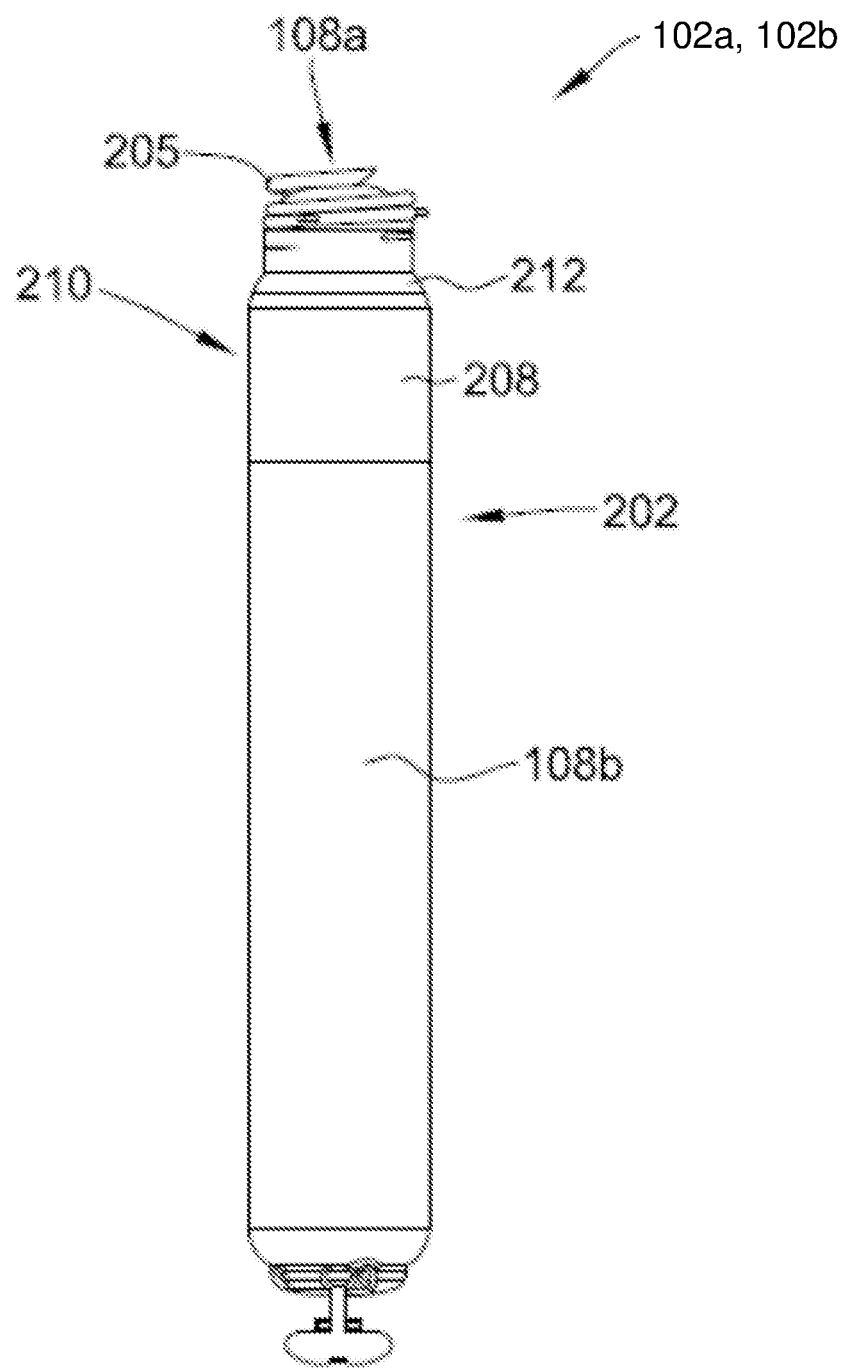
FIG. 2 illustrates a LP in accordance with certain embodiments herein.

FIG. 2 shows an LP 102a, 102b. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 1B.

The housing can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Exemplary Communication Receiver

Figure 3:
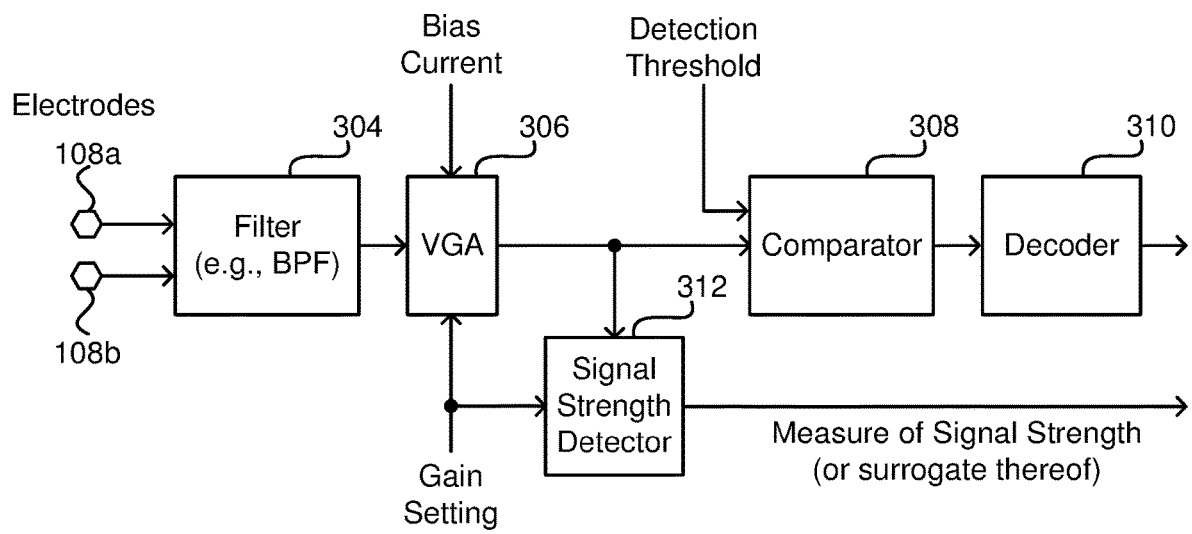
FIG. 3 is a block diagram of an exemplary communication receiver of an LP or other type of IMD.

FIG. 3 illustrates details of an exemplary communication receiver 302 of an LP (or other type of IMD) that can be used to receive i2i communication signals from another LP (or other type of IMD). The communication receiver 302 can also be used to receive communication signals from an external device, such as a programmer (e.g., 109 in FIG. 1A). Where communication is between multiple implantable medical devices (IMDs), such communication is referred to as implant-to-implant (i2i) communication, as noted above. Where communication is between an external programmer and an IMD, such communication can be referred to as programmer-to-implant (p2i) or implant-to-programmer (i2p) communication. The communication receiver 302 shown in and described with reference to FIG. 3 can be used, e.g., to implement the receiver 120 and/or the receiver 122 described above with reference to FIG. 1B. The communication receiver 302 can be used for both i2i communication, as well as p2i and i2p communication. However, most the following discussion relates to i2i communication, and techniques for reducing the amount of power that is consumed for i2i communication.

Referring to FIG. 3, the communication receiver 302, which is also referred to herein more succinctly as the receiver 302, is shown as including a filter 304, a variable gain amplifier (VGA) 306, a comparator 308, a decoder 310, and a signal strength detector 312. In FIG. 3 the signal strength detector 312 is shown as being part of the communication receiver 302. However, the signal strength detector 312 can alternatively be separate from the receiver, but communicatively coupled to the receiver such that it can measure the signal strength of i2i communication signals received by the receiver, or one or more surrogates thereof. Either way, the signal strength detector 312 should be communicatively coupled to a controller (e.g., 112) of the IMD so that it can provide measures of signal strength, or one or more surrogates thereof, to the controller.

In certain embodiments the filter 304 is a bandpass filter (BPF), but alternatively can be a low pass filter (LPF) and/or a high pass filter (HPF). The filter 304 filters the received communication signal to remove frequency components that are not of interest, and a filtered communication signal is provide to the VGA 306. The VGA 306 is used to amplify the filtered communication signal, in accordance with a gain setting and/or bias current, and outputs an amplified communication signal that is shown as being provided to the comparator 308. As shown in FIG. 3, the VGA 306 receives a bias current which effects the sensitivity of the receiver 302, i.e., increases in the bias current increase the sensitivity, and decreases in the bias current reduce the sensitivity. For example, the bias current can be used to adjust a gain of the VGA 306. Alternatively, or additionally, the gain of the VGA 306 can be controlled by a gain setting value. The magnitude of the bias current can be controlled via a bias current value that is stored in a register that is controlled by a controller, e.g., the controller 112 in FIG. 1B. Similarly, the magnitude of the gain setting can be controlled via a gain setting value that is stored in a register that is controlled by a controller, e.g., the controller 112 in FIG. 1B.

In accordance with certain embodiments, the VGA 306 is a switching amplifier, which is also known as a class-D amplifier, wherein the gain (and power consumption) of the amplifier can be adjusted by adjusting the switching frequency of the amplifier. More specifically, the gain (and power consumption) can be increased by increasing the switching frequency, and the gain (and power consumption) can be decreased by decreasing the switching frequency.

The comparator 308 is shown as comparing the amplified communication signal, output from the VGA 306, to a detection threshold. The output of the comparator 308 at any given time is either high or low, depending upon whether the amplified communication signal is greater than or less than the detection threshold. The detection threshold effects the sensitivity of the receiver 302, i.e., increases in the detection threshold decrease the sensitivity, and decreases in the detection threshold increase the sensitivity. The magnitude of the detection threshold can be controlled via a detection threshold value that is stored in a register that is controlled by a controller, e.g., the controller 112 in FIG. 1B. While changes to the detection threshold value change the sensitivity of the receive 302, changes to the detection threshold do not change the power consumption of the receiver 302. Since the detection threshold described above is being used to sense i2i communications, or more specifically, communication pulses thereof, the detection threshold may also be referred to more specifically as an i2i sense threshold. An exemplary value of an i2i sense threshold is 0.5 mV.

The output of the comparator 308 is provided to a decoder 310. The decoder 310 recovers data bits from the communication signal, and can also provide for synchronization. The output of the decoder 310 can be provided to a controller (e.g., 112 in FIG. 1B) that interprets the recovered data bits and if/when appropriate responds accordingly. For an example, the output of the decoder 310 can be used trigger a timer (e.g., a PVAB interval timer, a PVARP interval timer, an AV interval timer, an AAEI timer, or a VVEI timer that is used to cause a pacing pulse to be delivered at an appropriate time, but is not limited thereto.

In accordance with certain embodiments, the signal strength detector 312 is configured to measure the strength of one or more received i2i communication signals or one or more surrogates thereof. In accordance with certain embodiments, the signal strength detector 312 includes a peak detector circuit that is configured to detect a peak amplitude of the received communication signal, and a sample-and-hold (S/H) circuit that is configured to sample an output of the peak detector and provide such samples to a controller (e.g., 112 in FIG. 1B). Alternatively circuitry can be used for implementing the signal strength detector 312, as would be appreciated by one of ordinary skill in the art, and such alternative circuitry is within the scope of the embodiments described herein. Since the signal strength detector 312 includes circuitry that is configured to measure the strength of received i2i communication signals or one or more surrogates thereof, the signal strength detector 312 can also be referred to herein as measurement circuitry 312.

In FIG. 3, the receiver 302 is shown as being coupled to electrodes 108a and 108b to enable the receiver 302 to receiver conductive type communication signals from another IMD or an external device, such as an external programmer. The receiver 302 can alternatively be coupled to an antenna to receive radio frequency (RF) communication signals from another IMD or an external device. Alternatively, the receiver 302 can be coupled to a coil to receive inductive communication signals from another IMD or an external device. Other variations are also possible and within the scope of the embodiments described herein.

The receiver 302 can include alternative and/or additional components, depending upon implementation, as well as depending upon the specific type of communications signals it is intended to receiver. For example, the receiver can additionally include a low noise amplifier (LNA) upstream of the filter 304. The receiver may also include a mixer and a local oscillator that are used to down-convert a frequency of a received communication signal to a baseband. For still another example, it would be possible for the receiver 302 to include an analog-to-digital converter, e.g. in place of the comparator 308 and decoder 310. These are just a few examples of the communication receiver 302 which are not intended to be all encompassing.

Implant-to-Implant (i2i) Event Messaging

LPs 102a and 102b can utilize implant-to-implant (i2i) communication through event messages to coordinate operation with one another in various manners. The terms i2i communication, i2i event messages, and i2i event markers are used interchangeably herein to refer to event related messages and IMD/IMD operation related messages transmitted from an implanted device and directed to another implanted device (although external devices, e.g., a programmer, may also receive i2i event messages). In certain embodiments, LP 102a and LP 102b operate as two independent leadless pacers maintaining beat-to-beat dual-chamber functionality via a "Master/Slave" operational configuration. For descriptive purposes, the ventricular LP 102b shall be referred to as "vLP" and the atrial LP 102a shall be referred to as "aLP". LP 102a, 102b that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
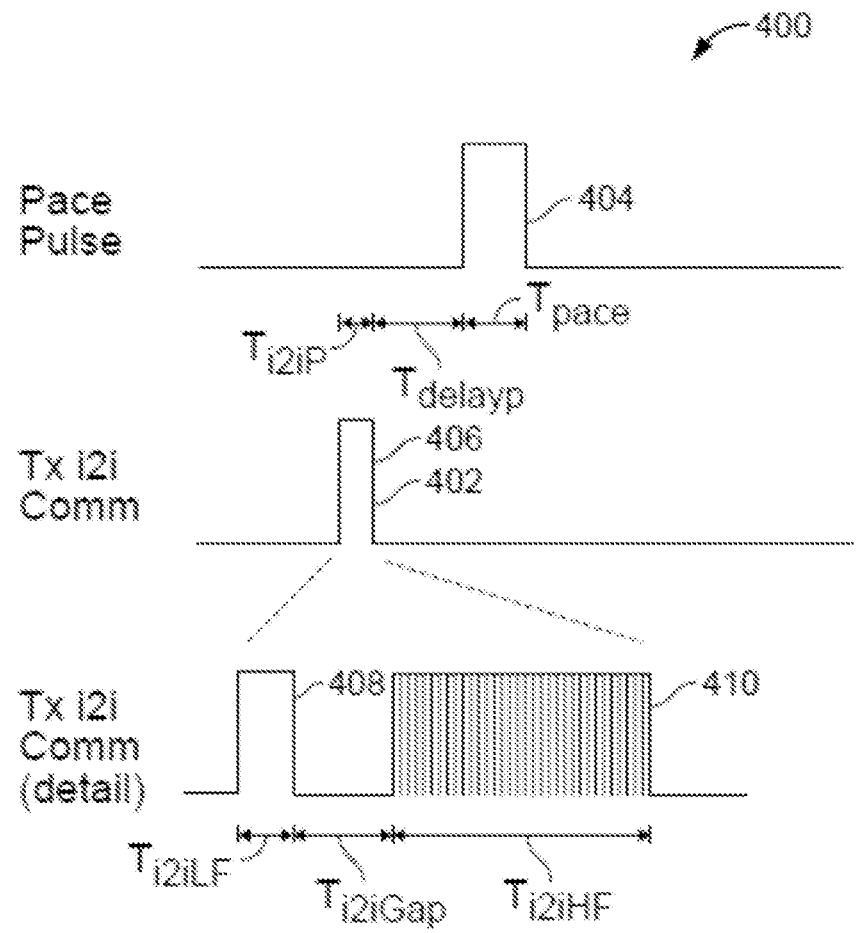
FIG. 4 is a timing diagram demonstrating one embodiment of implant to implant (i2i) communication for a paced event.

FIG. 4 is a timing diagram 400 demonstrating one example of an i2i communication for a paced event. The i2i communication may be transmitted, for example, from LP 102a to LP 102b. As shown in FIG. 4, in this embodiment, an i2i transmission 402 is sent prior to delivery of a pace pulse 404 by the transmitting LP (e.g., LP 102). This enables the receiving LP (e.g., LP 102b) to prepare for the remote delivery of the pace pulse. The i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period Ti2iLF, and high frequency pulse train 410 lasts for a period Ti2iHF. The end of low frequency pulse 408 and the beginning of high frequency pulse train 410 are separated by a gap period, Ti2iGap.

As shown in FIG. 4, the i2i transmission 402 lasts for a period Ti2iP, and pace pulse 404 lasts for a period Tpace. The end of i2i transmission 402 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means+/−10% of a specified value.

Figure 5:
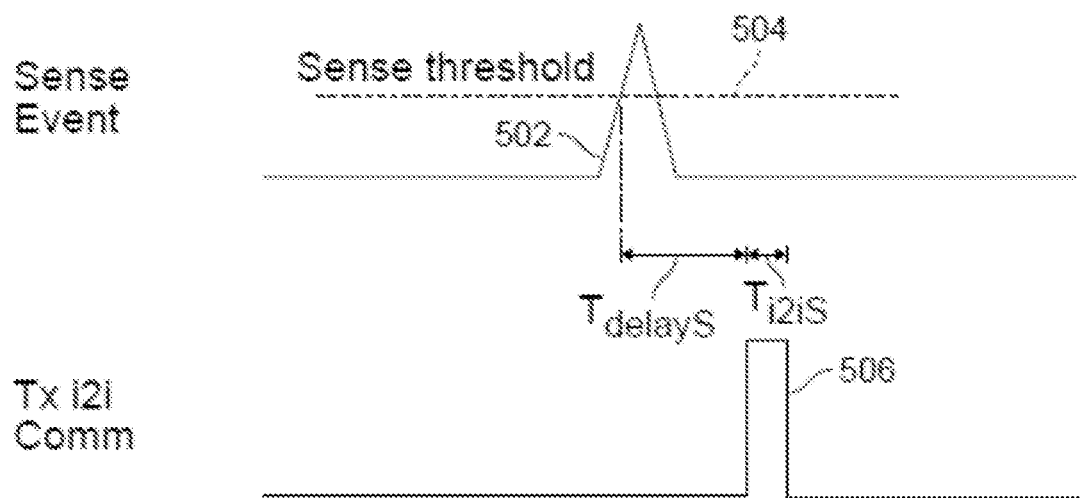
FIG. 5 is a timing diagram demonstrating one embodiment of i2i communication for a sensed event.

FIG. 5 is a timing diagram 500 demonstrating one example of an i2i communication for a sensed event. The i2i communication may be transmitted, for example, from LP 102a to LP 102b. As shown in FIG. 5, in this embodiment, the transmitting LP (e.g., LP 102) detects the sensed event when a sensed intrinsic activation 502 crosses a sense threshold 504. A predetermined delay period, TdelayS, after the detection, the transmitting LP transmits an i2i transmission 506 that lasts a predetermined period Ti2iS. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication can include event messages transmitted from the sensing/pacing electrodes at frequencies outside the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVAB or PVARP) |
| AP | Notification of a paced event in atrium | Initiate PAVB<br>Initiate AV interval (if not in PVARP) |

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB<br>Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a WI mode as the vLP does not depend on i2i communication to perform ventricular pace/sense activities. Once i2i communication is restored, the system 100 can automatically resume dual-chamber functionalities.

Dynamic Control of Wireless Communications Between IMDs

Figure 6:
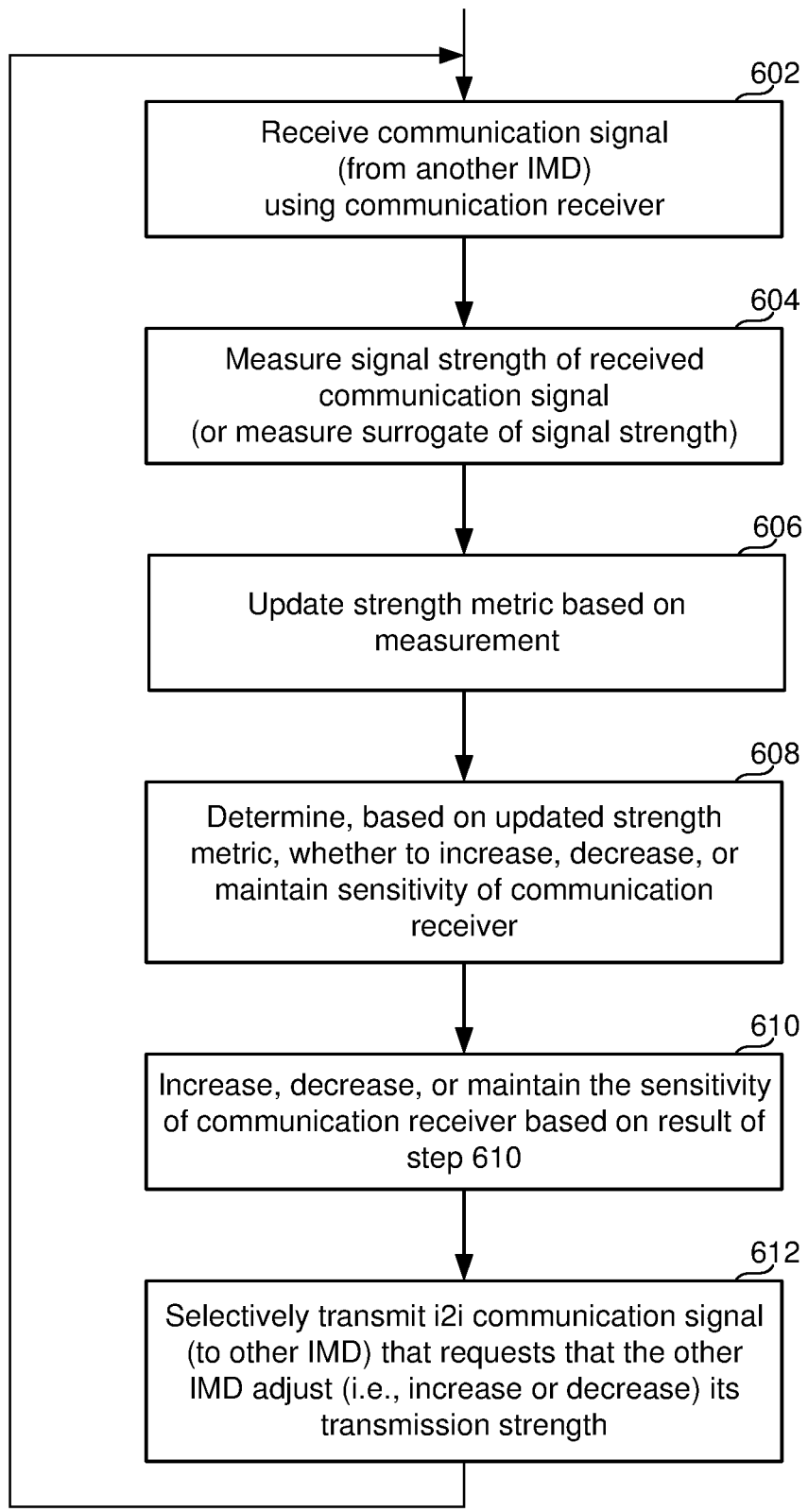
FIG. 6 is a high level flow diagram that is used to summarize methods according to various embodiments of the present technology that are for use by an IMD, such as an LP, and which methods can be used to dynamically control wireless communications between IMDs implanted within a patient.

Certain embodiments of the present technology will now be summarized with reference to the high level flow diagram of FIG. 6. Such methods can be used to adjust the amount of energy used by communication receivers of IMDs that wirelessly communicate with one another by providing dynamic control of the wireless communications between IMDs that are implanted within a patient. The methods described with reference to FIG. 6, as well as with reference to FIG. 3, are for use by an IMD that wirelessly communicates with another IMD.

Referring to FIG. 6, step 602 involves an IMD receiving one or more implant-to-implant (i2i) communication signals from the other IMD using a communication receiver of the IMD. Such an IMD can be, e.g., an LP (e.g., 102), but is not limited thereto. The communication receiver that is used to receive the i2i communication signal(s) at step 602 can be, e.g., the communication receiver 302, but is not limited thereto.

Still referring to FIG. 6, step 604 involves measuring a strength of at least one of the one or more received i2i communication signals or a surrogate thereof. The strength measured at step 604 can be a measure of amplitude of at least a portion of at least one of the one or more received i2i communication signals, or a magnitude of at least a portion of at least one of the one or more received i2i communication signals after rectification and integration thereof. The measure of amplitude can be, e.g., peak amplitude, peak-to-peak amplitude, average amplitude, root mean squared (RMS) amplitude, and/or like.

Alternatively, or additionally, the strength measured at step 604 can be a signal-to-noise ratio (SNR) of at least a portion of at least one of the one or more received i2i communication signals. Still another option is to measure a total energy of at least a portion of at least one of the one or more received i2i communication signals at step 604, or a specific part of such an i2i communication signal. An exemplary surrogate of signal strength that can be measured at step 604 is a bit-error-rate (BER) associated with at least a portion of at least one of the one or more received i2i communication signals. Where multiple different types of measures of strength (and/or surrogates thereof) are measured at step 604, such measures can be combined, e.g., using an equation that normalizes the various different types of measures and/or combines the different measures using a weighted average, or the like. Other variations are also possible and within the scope of the embodiments described herein.

Still referring to FIG. 6, step 606 involves updating a strength metric based on the strength measure or surrogate thereof obtained at a most recent instance of step 604. In accordance with certain embodiments, step 606 involves replacing a previous value of the strength metric with the strength or surrogate thereof measured at the most recent instance of step 604. Alternatively, step 606 can be performing by updating a moving average value of the strength metric using the measured strength or surrogate thereof. For example, such a moving average can be an average of the results of the five (or some other number of) most recent instances of step 604. In certain embodiments, the moving average can be a weighted moving average that weights more recent measures more than older measures. For example, where the moving average is an average of the five most recent instances, the most recent instance can be given the greatest weight (e.g., a weight of 5), the second most recent instance can be given the second greatest weight (e.g., a weight of 4), . . . and the fifth most recent instance can be given the least weight (e.g., a weight of 1). For still another example, the moving average can be an exponential moving average, which is a specific type of weighted moving average. Other variations are also possible and within the scope of the embodiments described herein.

Step 608 involves determining, based on the updated strength metric, whether to increase, decrease, or maintain the sensitivity of the communication receiver of the IMD. Step 610 involves increasing, decreasing, or maintaining the sensitivity of the communication receiver of the IMD (based on a result of step 608) in a manner that respectively increases, decreases, or maintains an energy usage level of the communication receiver. If it was determined at step 608 that the sensitivity of the communication receiver should be increased, then at step 610 the sensitivity of the communication receiver is increased in a manner that increases the energy usage level of the communication receiver, e.g., by increasing a gain, a bias current, and/or a switching frequency of an amplifier (e.g., 306) of the communication receiver (e.g., 302) of the IMD. If it was determined at step 608 that the sensitivity of the communication receiver should be decreased, then at step 610 the sensitivity of the communication receiver is decreased in a manner that decreases the sensitivity of the communication receiver, e.g., by decreasing a gain, a bias current, and/or a switching frequency of an amplifier (e.g., 306) of the communication receiver (e.g., 302) of the IMD. If it was determined at step 608 that the sensitivity of the communication receiver should be maintained, then at step 610 the sensitivity of the communication receiver is not adjusted, i.e., is maintained, e.g., by maintaining a gain, a bias current, and/or a switching frequency of an amplifier (e.g., 306) of the communication receiver (e.g., 302) of the IMD. Exemplary details of how steps 608 and 610 can be collectively performed, according to certain embodiments of the present technology, are discussed below with reference to FIGS. 7A and 7B.

Still referring to FIG. 6, in accordance with certain embodiments, at step 612 the IMD can selectively transmit, to the other IMD, an i2i communication signal that requests that the other IMD increase or decrease (i.e., adjusts) its transmission strength. Exemplary circumstances for which the IMD may request that the other IMD adjust its transmission strength are discussed below. In certain embodiments step 612 is optional and may not be performed.

Figure 7A:
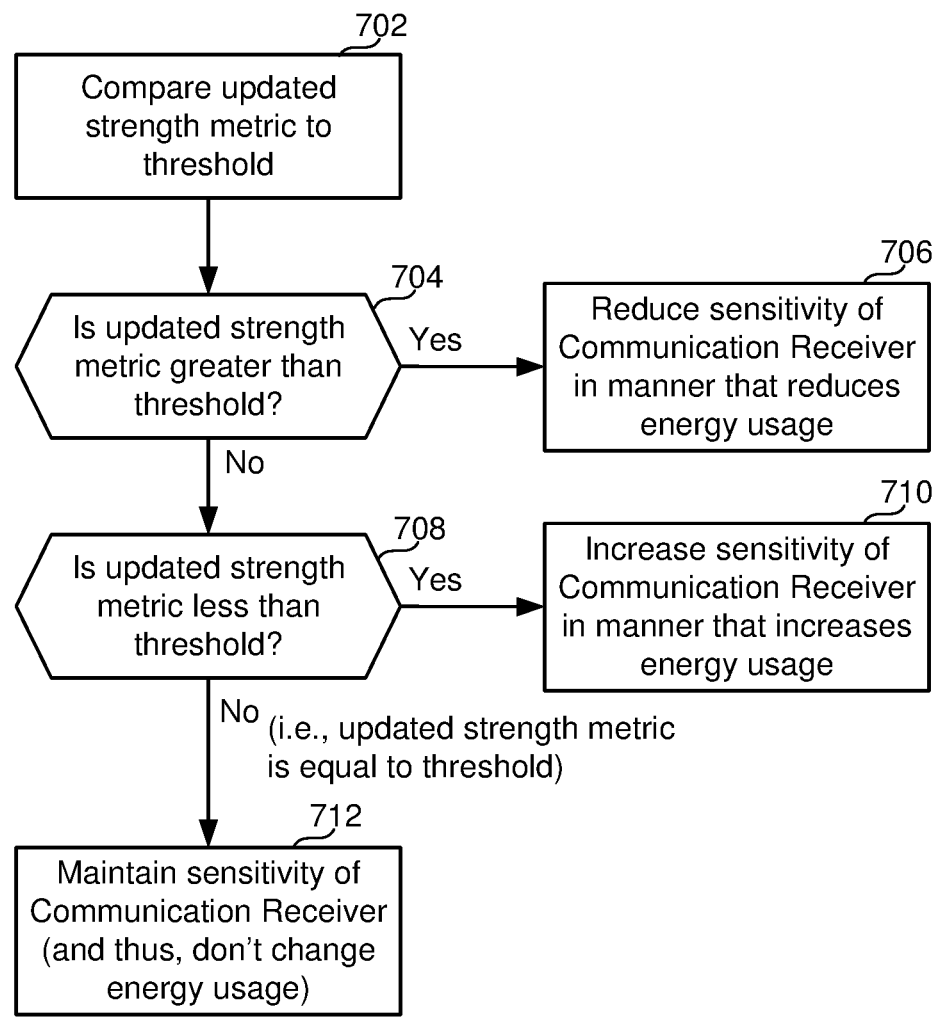
FIGS. 7A and 7B provide additional details of certain steps introduced in FIG. 6, according to certain embodiments of the present technology.

Exemplary details of how steps 608 and 610 can be collectively performed, according to certain embodiments of the present technology, are now discussed with reference to FIGS. 7A and 7B. Referring to FIG. 7A, step 702 involves comparing the updated strength metric (determined at step 606) to a threshold. At step 704 there is a determination of whether the updated strength metric is greater than the threshold. If the answer to the determination at step 704 is Yes, then flow goes to step 706 at which the sensitive of the communication receiver is reduced in a manner that reduces energy usage. If the answer to the determination at step 704 is No, then flow goes to step 708. At step 708 there is a determination of whether the updated strength metric is less than the threshold. If the answer to the determination at step 708 is Yes, then flow goes to step 710 at which the sensitive of the communication receiver is increased in a manner that increases energy usage. If the answer to the determination at step 708 is No, meaning the updated strength metric is equal to the threshold, then flow goes to step 712, at which the sensitive of the communication receiver is maintained. Following which ever one of steps 706, 710, or 712 is performed, flow then goes to step 612 (in FIG. 6), or if step 612 is not implemented flow can go from which ever one of steps 706, 710, or 712 is performed back to step 602 (in FIG. 6). Since nothing actively occurs at step 712, i.e., since it is implicit that the sensitivity of the communication receiver is maintained if it is neither increased nor decreased, step 712 need not be explicitly shown in the flow diagram. In the embodiments described with reference to FIG. 7A, at step 702 the updated strength metric was described as being compared to one threshold. In the embodiments described with reference to FIG. 7B, the updated strength metric is compared to more than one threshold. It is noted that the order of steps 704 and 708 (in FIG. 7A) can be reversed.

A variation on the embodiments described with reference to FIG. 7A, which variation still uses a single threshold, is as follows. At step 704 there is a determination of whether the updated strength metric is greater than the threshold by at least a specified percent (e.g., 10 percent); and at step 708 there is a determination of whether the updated strength metric is below the threshold by at least the specified percent (e.g., 10 percent). In such a variation, if the updated strength metric is at least the specified percent (e.g., 10 percent) above the threshold then the sensitivity is decreased, if the updated strength metric is at least the specified percent (e.g., 10 percent) below the threshold then the sensitivity is increased, and if the strength metric is within the specified percent (e.g., +/−10 percent) of the threshold the sensitivity is maintained (i.e., kept the same). Other variations are possible and within the scope of the embodiments described herein.

Figure 7B:
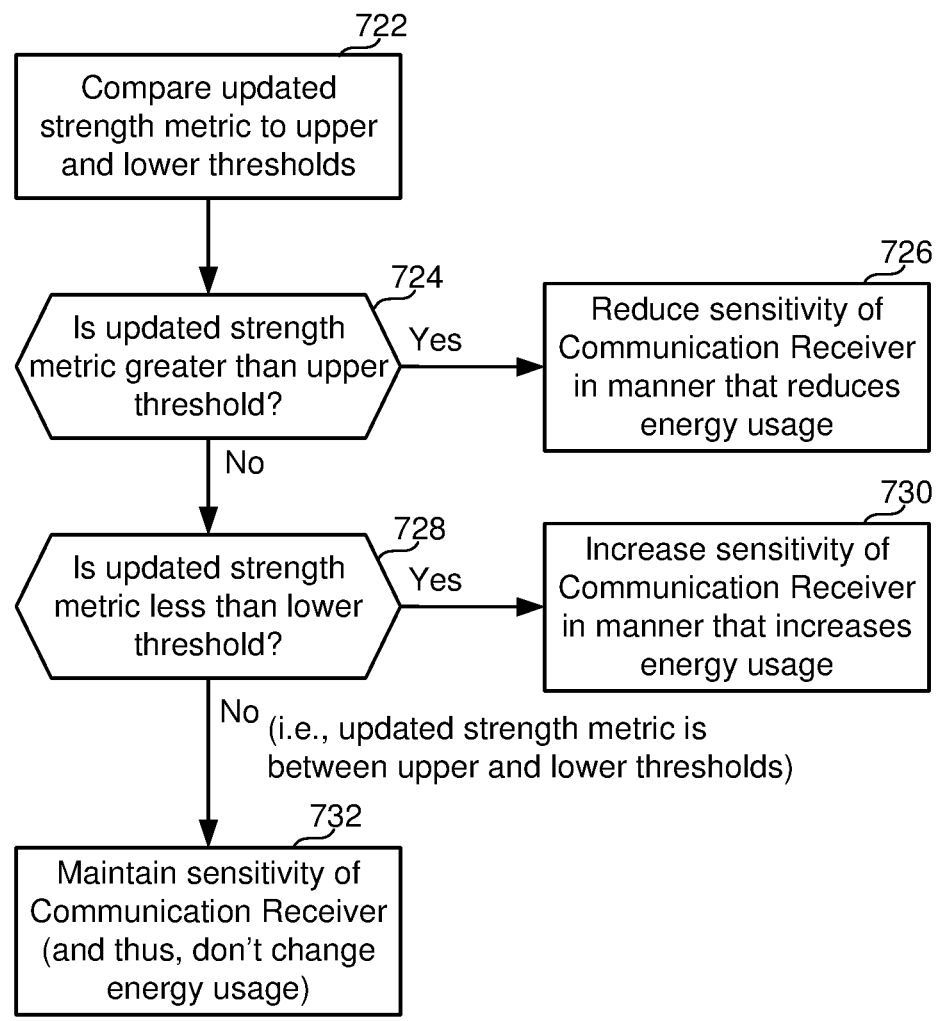

Referring to FIG. 7B, step 722 involves comparing the updated strength metric (determined at step 606) to an upper threshold and a lower threshold. At step 724 there is a determination of whether the updated strength metric is greater than the upper threshold. If the answer to the determination at step 724 is Yes, then flow goes to step 726 at which the sensitive of the communication receiver is reduced in a manner that reduces energy usage. If the answer to the determination at step 724 is No, then flow goes to step 728. At step 728 there is a determination of whether the updated strength metric is less than the lower threshold. If the answer to the determination at step 728 is Yes, then flow goes to step 730 at which the sensitive of the communication receiver is increased in a manner that increases energy usage. If the answer to the determination at step 728 is No, meaning the updated strength metric is between the upper and lower thresholds, inclusively, then flow goes to step 732, at which the sensitive of the communication receiver is maintained. Following which ever one of steps 726, 730, or 732 is performed, flow then goes to step 612. Since nothing actively occurs at step 732, i.e., since it is implicit that the sensitivity of the communication receiver is maintained if it is neither increased nor decreased, step 732 need not be explicitly shown in the flow diagram. It is noted that the order of steps 724 and 728 (in FIG. 7B) can be reversed.

In certain embodiments, the threshold used in the embodiments described with reference to FIG. 7A, or the upper and lower thresholds used in the embodiments described with reference to FIG. 7B, are preset during manufacturing or initialization of the IMD. In certain embodiments, the threshold used in the embodiments described with reference to FIG. 7A, or the upper and lower thresholds used in the embodiments described with reference to FIG. 7B, is/are set by a clinician or physician and are kept constant, at least until a clinician or physician decides to change the threshold (s), e.g., during a patient's visit with the clinician or physician. In other embodiments, the threshold used in the embodiments described with reference to FIG. 7A, or the upper and lower thresholds used in the embodiments described with reference to FIG. 7B, are dynamically and autonomously adjusted by the IMD. More specifically, in accordance with certain embodiments, the threshold used in the embodiments described with reference to FIG. 7A is adjusted based on an activity level and/or posture of the patient within which the IMD including the communication receiver is implanted. An activity level of the patient can be detected based on one or more signals produced by an accelerometer (e.g., 154 in FIG. 1B). Alternatively, or additionally, an activity level of the patient can be detected based on one or more signals produced by a temperature sensor (e.g., 152 in FIG. 1B). As noted above, alternatively, or additionally, a patient's activity level can be monitored based on their heart rate, as detected from an IEGM sensed using the electrodes (e.g., 108) and/or sensed using a plethysmography signal obtained using a plethysmography sensor and/or sensed using a heart sound signal obtained using a heart sound sensor (not shown), but not limited thereto.

It is typically more important to provide appropriate cardiac synchrony when a patient is exercising, compared to if the patient is at rest. Accordingly, when a patient is determined to be active, the threshold(s) used in FIGS. 7A and 7B can be increased from baseline setting(s) to thereby increase the probability that i2i communication is successful while the patient is exercising (at the expense of more energy being used). Thereafter, when it is determined that the patient has stopped exercising, the threshold(s) used in FIGS. 7A and 7B can be decreased back to their baseline setting(s) (in order to conserve energy). More generally, an activity level of a patient and/or a surrogate thereof can be monitored, and at least one of the one or more thresholds to which the updated strength metric is/are compared (e.g., at step 702 or 722) can be adjusted based on the activity level of the patient or the surrogate thereof. So as to distinguish the thresholds referred to in FIGS. 7A and 7B from the detection threshold referred to with reference to FIG. 3, the thresholds referred to in FIGS. 7A and 7B can be referred to more specifically as strength thresholds.

It would also be possible to adjust one or more strength thresholds based on whether a patient is lying down or sitting or standing upright. If a patient is lying down, as can be detected using an accelerometer (e.g., 154), the patient is likely at rest and may even be sleeping. By contrast, if a patient is sitting or standing upright, as can be detected using the accelerometer (e.g., 154), the patient is likely to be somewhat more active compared to if they are lying down. Accordingly, the strength threshold(s) used when a patient is lying down can be adjusted to be lower than the strength threshold(s) used with the patient is sitting or standing upright. Other variations are also possible and within the scope of the embodiments described herein. For example, other types of sensors can be used in place of an accelerometer and/or in addition to an accelerometer to detect a posture and/or activity level of a patient.

In the embodiments of the present technology described above with reference to FIGS. 6, 7A and 7B, various different ways of adjusting the sensitivity of a communication receiver of an IMD were discussed, as were various different ways in which it can be determined whether the sensitivity of the communication receiver should be increased, decreased or maintained. In order to ensure that various components of a communication receiver operate correctly (e.g., without being saturated, or the like), and/or to try to ensure that at least some minimal level of i2i communication is maintained, the sensitivity of the communication receiver of an IMD may only be adjustable within a sensitivity range that includes a minimum sensitivity setting and a maximum sensitivity setting. In accordance with certain embodiments, when the communication receiver is already at its maximum sensitivity setting and the result of step 610 (and/or step 710 or step 730) is that the sensitivity of the communication receiver is to be increased, instead of the IMD doing nothing or increasing its sensitivity such that it exceeds its maximum setting, the IMD can instead transmit an i2i communication signal to another IMD (with which it is communication) that requests that the other IMD increase a strength of one or more future i2i communication signals that will be transmitted by the other IMD to the IMD. Conversely, when the communication receiver of the IMD is already at its minimum sensitivity setting and the result of step 610 (and/or step 706 or step 726) is that the sensitivity of the communication receiver is to be decreased, instead of the IMD doing nothing or decreasing its sensitivity such that it falls below its minimum setting, the IMD can instead transmit an i2i communication signal to the other IMD (with which it is communicating) that requests that the other IMD decrease a strength of one or more future i2i communication signals that will be transmitted by the other IMD to the IMD. Referring back to FIG. 6, such requests that are sent by one IMD to another IMD, to request that the other IMD adjust (i.e., increase or decrease) its transmission strength, can occur at instances of step 612.

In accordance with certain embodiments, an IMD may also request that another IMD adjusts its transmission strength even if the IMD is not at its minimum or maximum sensitivity setting, e.g., if the IMD determines that an energy cost of the other IMD increasing its transmission strength is less than the energy cost of the IMD increasing the sensitivity of its communication receiver. Alternatively, or additionally, an IMD may also request that another IMD increase its transmission strength even if the IMD is not at its minimum sensitivity setting if the IMD detects external noise (either measured by the communication receiver directly, or indirectly detected as messages with errors). These are additional examples of how step 612 in FIG. 6 may be performed.

In accordance with certain embodiments of the present technology, a communication receiver (e.g., 302) of an IMD (e.g., 102a) can have a minimum acceptable signal-to-noise ratio (SNR) associated with it, e.g., as specified by a manufacturer, a clinician or physician. Whenever such an IMD (e.g., 102a) is communicating with another IMD (e.g., 102b) using i2i communication signals, there will be a combination of a level of the sensitivity of the communication receiver of the IMD (e.g., 102a) that receives i2i communication signals from the other IMD (e.g., 102b), and a level of transmitter strength associated with the other IMD (e.g., 102b) from which the IMD (e.g., 102a) receives i2i communication signals. In accordance with certain such embodiments, when the IMD (e.g., 102a) is determining whether to increase, decrease, or maintain the sensitivity of its communication receiver, the IMD may determine whether there is another combination of the level of the sensitivity of its communication receiver (that receives i2i communication signals from the other IMD), and the level of transmitter strength associated with the other IMD from which the IMD receives i2i communication signals, that will reduce a total system energy usage while satisfying the minimum acceptable SNR associated with the communication receiver. When it is determined that there is another combination (that will reduce the total system energy usage while satisfying the minimum acceptable SNR), in order to implement the other combination and thereby reduce the total system energy usage while still satisfying the minimum acceptable SNR, the IMD (e.g., 102a) may modify the sensitivity of its communication receiver and/or may transmit an i2i communication signal to the other IMD (e.g., 102b) that requests that the other IMD modify the strength of one or more future i2i communication signals. In such an embodiment, it would be preferable that a transmission strength is not increased to the point that it may cause inadvertent capture of a patient's heart. This can be achieved by specifying a maximum transmission strength, which may vary in dependence in a dynamic capture threshold, e.g., the maximum transmission strength may be kept at least some specified margin below the capture threshold. In accordance with an embodiment, a manufacturer determines and pre-specifies the best pairings of transmission and reception i2i settings that achieve the most efficient energy usage at each settings level, and the IMDs step up/down these prespecified settings as needed to satisfy the minimum acceptable SNR with the most efficient pairing possible, optionally using hysteresis. In still another embodiment, an external programmer (that wirelessly communicates with an IMD) determines these pairings levels, which can optionally be dependent on the load impedance of each IMD (and thus the energy for each i2i transmission output would change). Still other variations are possible and within the scope of the embodiments described herein.

In accordance with certain embodiments, where an IMD expects its communication receiver to receive an i2i communication signal within a window, and fails to receive the i2i communication signal within the window, a controller (e.g., 112) of the IMD can surmise that the failure to receive the i2i communication signal was likely because the sensitivity of its communication receiver was set too low, and in response thereto, can increase the sensitivity of its communication receiver and/or cause an i2i communication signal to be sent to the other IMD requesting that it increase its transmission strength. More generally, an IMD (e.g., 102a) can detect when it is likely that another IMD (e.g., 102b) transmitted an i2i communication signal that was not received by the communication receiver of the IMD (102a). Then, in response to the IMD (e.g., 102a) detecting that it is likely that the other IMD (e.g., 102b) transmitted an i2i communication signal that was not received by the communication receiver of the IMD (e.g., 102a), the IMD (e.g., 102a) may increase its sensitivity and/or may transmit an i2i communication signal to the other IMD (e.g., 102b) that requests that the other IMD (e.g., 102b) modify the strength of one or more future i2i communication signals that will be transmitted by the other IMD (e.g., 102b) to the IMD (e.g., 102a). There are various different ways that a controller of an IMD can detect when it is likely that another IMD transmitted an i2i communication signal that was not received by the communication receiver of the IMD, one example of which was discussed above. For another example, if a pair of IMDs are configured to communicate with one another once per cardiac cycle, one of the IMDs can detect that is likely that the other IMD transmitted an i2i communication signal that was not received by the communication receiver of the IMD if one or more cardiac cycles have occurred without the communication receiver receiving an i2i communication signal from the other IMD. Various other techniques are possible (for detecting when it is likely that another IMD transmitted an i2i communication signal that was not received by the communication receiver of the IMD) and within the scope of the embodiments described herein.

There may be various different types of i2i communication signals that IMDs may transmit to one another. For example, certain i2i communication signals, which inform another IMD of paced or sensed events, or the like, may be used to control delivery of therapy. Other i2i communication signals may be transmitted between a pair of IMDs solely for the purpose of determining whether one or both of the IMDs should adjust their sensitivity. For the purpose of this discussion, i2i communication signals that are for use in controlling delivery of therapy can be referred to as primary i2i communication signals, and i2i communication signals for use in controlling the sensitivity of a communication receiver of the IMD can be referred to as secondary i2i communication signals. Most likely the primary i2i communication signals will be transmitted more often than the secondary i2i communication signals. For example, one or more primary i2i communication signals may be transmitted every cardiac cycle, while secondary i2i communication signals may be transmitted much less frequently, e.g., once every sixty cardiac cycles or once per minute, but not limited thereto. For another example, rather than transmitting secondary i2i communication signals on a fixed cycle or schedule, secondary i2i communication signals may be transmitted "on demand" when an IMD determines that there is a need to adjust the sensitivity of a communication receiver, or more generally, when needed to communicate a request to make a change to an i2i communication setting. Referring back to the high level flow diagram of FIG. 6, in accordance with certain embodiments, the signal strength that is being measured at instances of step 604 can be the signal strength of secondary i2i communication signals. In other embodiments, there are no secondary i2i communication signals, and it is the strength of primary i2i communication signals that are being measured at instances of step 604. However, where this is the case, the strength of every received i2i communication signal need not be measured. Rather, it may be the that only the strength of every Nth (e.g., 5th, or 10th) i2i communication signal is measured. Alternatively, it would also be possible to measure the strength of every i2i communication signal received by a communication receiver.

In accordance with certain embodiments, a scheme is used to evaluate a relative margin of an i2i communication channel. In such embodiments, an i2i communication is periodically and purposefully weakened (either by decreasing the strength of the signal transmitted from a first IMD by a defined amount [absolute or relative], or by decreasing the sensitivity of the receiver of a second IMD by a defined amount [absolute or relative]), and the received strength of that weakened communication signal is measured, or the lack of a received signal is noted, whereby both results provide an indication of the relative margin available. The strength of the primary signal can then be increased, decreased, or maintained the same based on the results and a determined or specified minimum margin requirement. This weakened signal can be applied directly to primary communication signals, or the weakened signal could be implemented as a secondary "margin-test-only" transmission signal that, for example, could be transmitted some interval after a primary communication signal. This approach can be further expanded by transmitting more than one secondary transmission signal, with each of these secondary signals transmitted at different transmission strengths across a range of transmission strengths. In this way, the receiving IMD (the second IMD) will be able to more-quickly assess the extent of available margin across a broad spectrum of transmission strengths.

Where multiple IMDs (e.g., LPs 102a and 102b) are implanted within a patient, the orientation of the IMDs may change relative to one another over time. This is especially the case where IMDs are implanted within cardiac chambers of a patient's heart, since cardiac chambers contract and expand throughout each cardiac cycle. Accordingly, where LPs or other IMDs are implanted within or are attached to cardiac chambers, the orientations of the IMDs relatively to one another will likely vary through each cardiac cycle, through each respiratory cycle, and/or due to changes in posture. Certain relative orientations may provide for better i2i communications that others. Indeed, it may even be possible that during portions of a cardiac cycle LPs or other IMDs cannot successfully communicate or "hear" one another using i2i communications even though they are attempting to communicate or "talk" with one another using i2i communications. When this is the case, the IMDs can be said to be within a "deaf zone."

Tests can be performed to determine at what time within a cardiac cycle an i2i communication signal can be transmitted by an LP (or other IMD) such that another LP (or other IMD) can receive i2i communication signal at a low sensitivity setting that conserves power. Thereafter, the LP (or other IMD) can be configured to time its transmitting of i2i communication signals such that i2i communication signals are transmitted during specific times within cardiac cycles, e.g., at a specific delay following a specific sensed or paced event, or the like. In certain embodiments, when step 604 and/or 606 is/are performed by an IMD (e.g., LP 102a), the IMD can take into account where within individual cardiac cycles different i2i communication signals are received. Additionally, the IMD (e.g., LP 102a) can determine whether an adjustment should be made to when the other IMD (e.g., LP 102b) transmits i2i communication signals within cardiac cycles, to thereby enable the IMD (e.g., 102a) to reduce the sensitivity and energy usage of its communication receiver (e.g., 302). In such a case, the IMD (e.g., 102a) can transmit an i2i communication signal to the other IMD (e.g., 102b) requesting that the other IMD adjust when the other IMD (e.g., 102b) transmits i2i communication signals within individual cardiac cycles to thereby enable the IMD (e.g., 102a) to reduce the sensitivity and energy usage of the communication receiver (e.g., 302) of the IMD (e.g., 102a).

Figure 8:
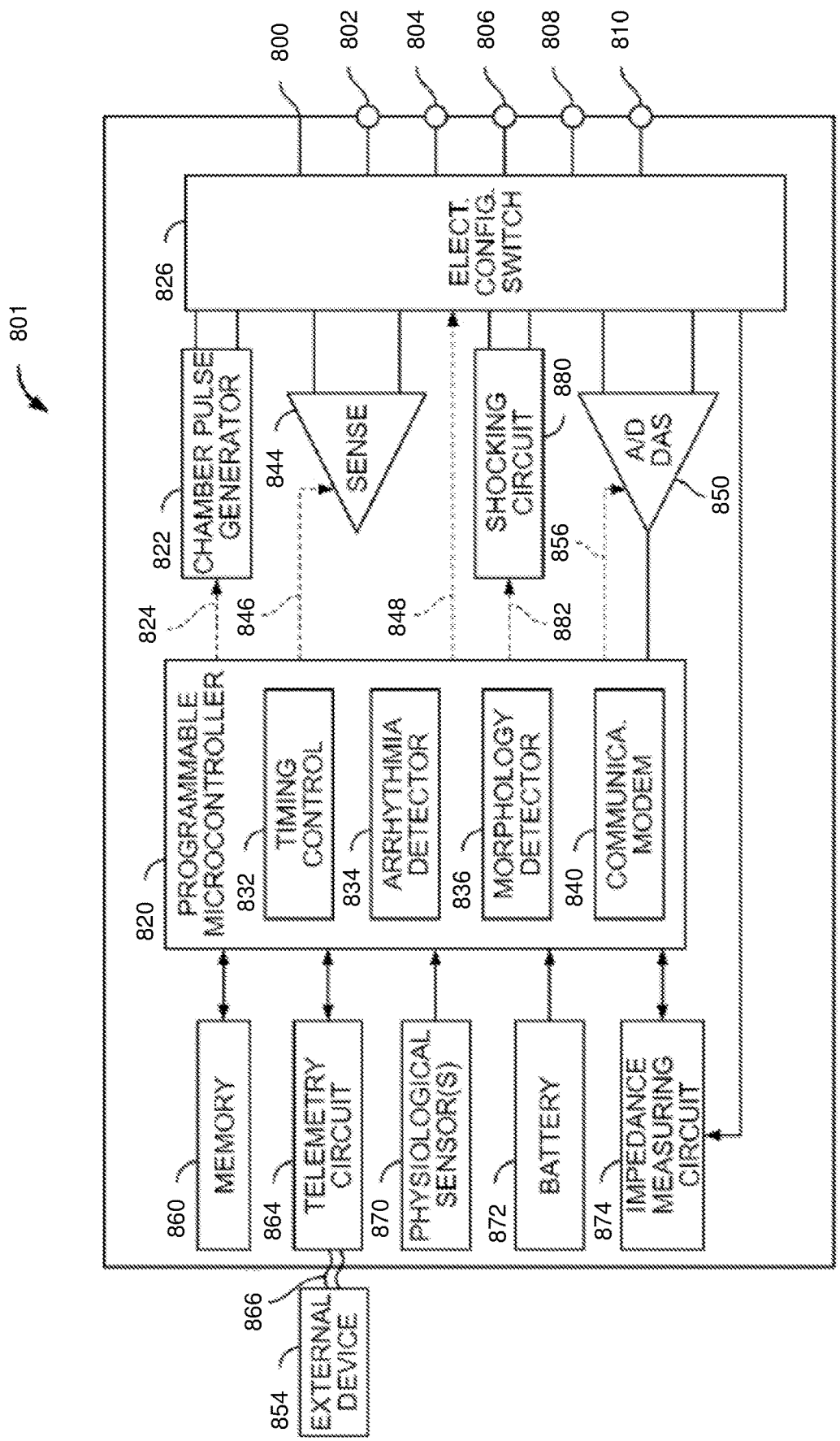
FIG. 8 shows a block diagram of one embodiment of an IMD that is implanted into the patient as part of the implantable cardiac system in accordance with certain embodiments herein.

FIG. 8 shows a block diagram of one embodiment of an IMD (e.g., LP) 801 that is implanted into the patient as part of the implantable cardiac system in accordance with certain embodiments herein. IMD 801 may be implemented as a full-function biventricular pacemaker, equipped with both atrial and ventricular sensing and pacing circuitry for four chamber sensing and stimulation therapy (including both pacing and shock treatment). Optionally, IMD 801 may provide full-function cardiac resynchronization therapy. Alternatively, IMD 801 may be implemented with a reduced set of functions and components. For instance, the IMD may be implemented without ventricular sensing and pacing.

IMD 801 has a housing 800 to hold the electronic/computing components. Housing 800 (which is often referred to as the "can", "case", "encasing", or "case electrode") may be programmably selected to act as the return electrode for certain stimulus modes. Housing 800 may further include a connector (not shown) with a plurality of terminals 802, 804, 806, 808, and 810. The terminals may be connected to electrodes that are located in various locations on housing 800 or elsewhere within and about the heart. IMD 801 includes a programmable microcontroller 820 that controls various operations of IMD 801, including cardiac monitoring and stimulation therapy. Microcontroller 820 includes a microprocessor (or equivalent control circuitry), RAM and/or ROM memory, logic and timing circuitry, state machine circuitry, and I/O circuitry.

IMD 801 further includes a first pulse generator 822 that generates stimulation pulses for delivery by one or more electrodes coupled thereto. Pulse generator 822 is controlled by microcontroller 820 via control signal 824. Pulse generator 822 may be coupled to the select electrode(s) via an electrode configuration switch 826, which includes multiple switches for connecting the desired electrodes to the appropriate I/O circuits, thereby facilitating electrode programmability. Switch 826 is controlled by a control signal 828 from microcontroller 820.

In the embodiment of FIG. 8, a single pulse generator 822 is illustrated. Optionally, the IMD may include multiple pulse generators, similar to pulse generator 822, where each pulse generator is coupled to one or more electrodes and controlled by microcontroller 820 to deliver select stimulus pulse(s) to the corresponding one or more electrodes.

Microcontroller 820 is illustrated as including timing control circuitry 832 to control the timing of the stimulation pulses (e.g., pacing rate, AV delay, AAEI, VVEI, etc.). Timing control circuitry 832 may also be used for the timing of refractory periods, blanking intervals, noise detection windows, evoked response windows, alert intervals, marker channel timing, and so on. Microcontroller 820 may also have an arrhythmia detector 834 for detecting arrhythmia conditions and a morphology detector 836. Although not shown, the microcontroller 820 may further include other dedicated circuitry and/or firmware/software components that assist in monitoring various conditions of the patient's heart and managing pacing therapies. The microcontroller can include a processor. The microcontroller, and/or the processor thereof, can be used to perform the methods of the present technology described herein.

IMD 801 is further equipped with a communication modem (modulator/demodulator) 840 to enable wireless communication with the remote slave pacing unit. Modem 840 may include one or more transmitters and two or more receivers as discussed herein in connection with FIG. 1B. In one implementation, modem 840 may use low or high frequency modulation. As one example, modem 840 may transmit i2i messages and other signals through conductive communication between a pair of electrodes. Modem 840 may be implemented in hardware as part of microcontroller 820, or as software/firmware instructions programmed into and executed by microcontroller 820. Alternatively, modem 840 may reside separately from the microcontroller as a standalone component.

IMD 801 includes a sensing circuit 844 selectively coupled to one or more electrodes, that perform sensing operations, through switch 826 to detect the presence of cardiac activity in the right chambers of the heart. Sensing circuit 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of sensing circuit 844 is connected to microcontroller 820 which, in turn, triggers or inhibits the pulse generator 822 in response to the presence or absence of cardiac activity. Sensing circuit 844 receives a control signal 846 from microcontroller 820 for purposes of controlling the gain, threshold, polarization charge removal circuitry (not shown), and the timing of any blocking circuitry (not shown) coupled to the inputs of the sensing circuitry.

In the embodiment of FIG. 8, a single sensing circuit 844 is illustrated. Optionally, the IMD may include multiple sensing circuits, similar to sensing circuit 844, where each sensing circuit is coupled to one or more electrodes and controlled by microcontroller 820 to sense electrical activity detected at the corresponding one or more electrodes. Sensing circuit 844 may operate in a unipolar sensing configuration or in a bipolar sensing configuration.

IMD 801 further includes an analog-to-digital (ND) data acquisition system (DAS) 850 coupled to one or more electrodes via switch 826 to sample cardiac signals across any pair of desired electrodes. Data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). Data acquisition system 850 is controlled by a control signal 856 from the microcontroller 820.

Microcontroller 820 is coupled to a memory 860 by a suitable data/address bus. The programmable operating parameters used by microcontroller 820 are stored in memory 860 and used to customize the operation of IMD 801 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of IMD 801 may be non-invasively programmed into memory 860 through a telemetry circuit 864 in telemetric communication via communication link 866 with external device 854. Telemetry circuit 864 allows intracardiac electrograms and status information relating to the operation of IMD 801 (as contained in microcontroller 820 or memory 860) to be sent to external device 854 through communication link 866.

IMD 801 can further include magnet detection circuitry (not shown), coupled to microcontroller 820, to detect when a magnet is placed over the unit. A magnet may be used by a clinician to perform various test functions of IMD 801 and/or to signal microcontroller 820 that external device 854 is in place to receive or transmit data to microcontroller 820 through telemetry circuits 864.

IMD 801 can further include one or more physiological sensors 870.

Such sensors are commonly referred to as "rate-responsive" sensors because they are typically used to adjust pacing stimulation rates according to the exercise state of the patient. However, physiological sensor 870 may further be used to detect changes in cardiac output, changes in the physiological condition of the heart, or diurnal changes in activity (e.g., detecting sleep and wake states). Signals generated by physiological sensors 870 are passed to microcontroller 820 for analysis. Microcontroller 820 responds by adjusting the various pacing parameters (such as rate, AV Delay, AAEI, VVEI, etc.) at which the atrial and ventricular pacing pulses are administered. While shown as being included within IMD 801, physiological sensor(s) 870 may be external to IMD 801, yet still be implanted within or carried by the patient. Examples of physiologic sensors might include sensors that, for example, sense respiration rate, pH of blood, ventricular gradient, activity, position/posture, minute ventilation (MV), and so forth. Referring briefly back to FIG. 1B, other exemplary types of physiologic sensors include a temperature sensor (e.g., 152) and an accelerometer (e.g., 154).

A battery 872 provides operating power to all of the components in IMD 801. Battery 872 is preferably capable of operating at low current drains for long periods of time, may be capable of providing high-current pulses (for capacitor charging) when the patient requires a shock pulse (e.g., in excess of 2 A, at voltages above 2 V, for periods of 10 seconds or more). Battery 872 also desirably has a predictable discharge characteristic so that elective replacement time can be detected. As examples, the IMD 801 may employ a lithium/carbon monofluoride (Li/CFx) battery, or a lithium/silver vanadium oxide battery, but is not limited thereto.

IMD 801 further includes an impedance measuring circuit 874, which can be used for many things, including: detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 874 is coupled to switch 826 so that any desired electrode may be used. In this embodiment IMD 801 further includes a shocking circuit 880 coupled to microcontroller 820 by a data/address bus 882.

While many of the embodiments of the present technology described above have been described as being for use with LP type IMDs, embodiments of the present technology that are for use in reducing how often a first receiver of an IMD wakes up a second receiver of an IMD, in order to reduce power consumption, can also be used with other types of IMDs besides an LP. Accordingly, unless specifically limited to use with an LP, the claims should not be limited to use with LP type IMDs. For example, embodiments of the present technology can also be used with a subcutaneous-ICD and/or a subcutaneous pacemaker, but are not limited thereto.

While the embodiments of the present technology described herein are primarily described as being used with IMDs that utilize conductive communication, such embodiments can alternatively be used with IMDs that utilize other types of wireless communication, such as, but not limited to, radio frequency (RF) communication or inductive communication.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed embodiments. For example, it would be possible to combine or separate some of the steps shown in FIGS. 6, 7A and 7B. For another example, it is possible to change the boundaries of some of the blocks shown in FIGS. 1B, 3 and 8.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use by an implantable medical device (IMD) that wirelessly communicates with another IMD, the method comprising:
    receiving one or more implant-to-implant (i2i) communication signals from the other IMD using a communication receiver of the IMD;
    measuring a strength of at least one of the one or more received i2i communication signals or a surrogate thereof;
    updating a strength metric based on the measured strength or the surrogate thereof;
    comparing the updated strength metric to one or more thresholds;
    determining whether to increase, decrease, or maintain a sensitivity of a communication receiver of the IMD based on a result of the comparing;
    selectively increasing, decreasing, or maintaining the sensitivity of the communication receiver of the IMD, based on a result of the determining, in a manner that respectively increases, decreases, or maintains an energy usage level of the communication receiver;
    monitoring at least one of an activity level or a surrogate thereof of a patient within which the IMD is implanted; and
    selectively adjusting at least one of the one or more thresholds to which the updated strength metric is/are compared, the selectively adjusting performed based on the activity level of the patient or the surrogate thereof.

2. The method of claim 1, wherein the communication receiver includes an amplifier:
    when the result of the determining is that the sensitivity of the communication receiver of the IMD is to be increased, the increasing the sensitivity of the communication receiver of the IMD, in a manner that increases the energy usage level of the communication receiver of the IMD, comprises increasing at least one of a gain, a bias current, or a switching frequency of the amplifier of the communication receiver of the IMD; and
    when the result of the determining is that the sensitivity of the communication receiver of the IMD is to be decreased, the decreasing the sensitivity of the communication receiver of the IMD, in a manner that decreases the energy usage level of the communication receiver of the IMD, comprises decreasing at least one of a gain, a bias current, or a switching frequency of the amplifier of the communication receiver of the IMD.

3. The method of claim 1, wherein the strength of at least one of the one or more received i2i communication signals or the surrogate thereof that is measured and used to update the strength metric is indicative of at least one of the following:
    a measure of amplitude of at least a portion of at least one of the one or more received i2i communication signals;
    a magnitude of at least a portion of at least one of the one or more received i2i communication signals after rectification and integration thereof;
    a signal-to-noise ratio (SNR) of at least a portion of at least one of the one or more received i2i communication signals;
    a total energy of at least a portion of at least one of the one or more received i2i communication signals; or
    a bit-error-rate (BER) associated with at least a portion of at least one of the one or more received i2i communication signals.

4. The method of claim 1, wherein the updating the strength metric based on the measured strength or the surrogate thereof comprises:
    replacing a previous value of the strength metric with the measured strength or the surrogate thereof; or
    updating a moving average value of the strength metric using the measured strength or the surrogate thereof.

5. A method for use by an implantable medical device (IMD) that wirelessly communicates with another IMD, the method comprising:
    receiving one or more implant-to-implant (i2i) communication signals from the other IMD using a communication receiver of the IMD;

measuring a strength of at least one of the one or more received i2i communication signals or a surrogate thereof;

updating a strength metric based on the measured strength or the surrogate thereof;

determining, based on the updated strength metric, whether to increase, decrease, or maintain a sensitivity of the communication receiver of the IMD; and selectively increasing, decreasing, or maintaining a sensitivity of the communication receiver of the IMD, based on a result of the determining, in a manner that respectively increases, decreases, or maintains an energy usage level of the communication receiver;

wherein the sensitivity of the communication receiver of the IMD is adjustable within a sensitivity range that includes a minimum sensitivity setting and a maximum sensitivity setting;

wherein when the communication receiver is already at the maximum sensitivity setting and the result of the determining is that the sensitivity of the communication receiver is to be increased, the IMD transmits an i2i communication signal to the other IMD that requests that the other IMD increase a strength of one or more future i2i communication signals that will be transmitted by the other IMD to the IMD; and wherein when the communication receiver is already at the minimum sensitivity setting and the result of the determining is that the sensitivity of the communication receiver is to be decreased, the IMD transmits an i2i communication signal to the other IMD that requests that the other IMD decrease a strength of one or more future i2i communication signals that will be transmitted by the other IMD to the IMD.

6. The method of claim 5, wherein the updating the strength metric based on the measured strength or the surrogate thereof comprises:

replacing a previous value of the strength metric with the measured strength or the surrogate thereof; or updating a moving average value of the strength metric using the measured strength or the surrogate thereof.

7. A method for use by an implantable medical device (IMD) that wirelessly communicates with another IMD, the method comprising:

receiving one or more implant-to-implant (i2i) communication signals from the other IMD using a communication receiver of the IMD;

measuring a strength of at least one of the one or more received i2i communication signals or a surrogate thereof;

updating a strength metric based on the measured strength or the surrogate thereof;

determining, based on the updated strength metric, whether to increase, decrease, or maintain a sensitivity of the communication receiver of the IMD; and selectively increasing, decreasing, or maintaining the sensitivity of the communication receiver of the IMD, based on a result of the determining, in a manner that respectively increases, decreases, or maintains an energy usage level of the communication receiver;

wherein the communication receiver of the IMD has a minimum acceptable signal-to-noise ratio (SNR) associated with the communication receiver of the IMD;

wherein at any given time there is a combination of a level of the sensitivity of the communication receiver that receives i2i communication signals from the other IMD, and a level of transmitter strength associated with the other IMD from which the IMD receives i2i communication signals;

wherein the determining, based on the updated strength metric, whether to increase, decrease, or maintain the sensitivity of the communication receiver of the IMD comprises determining whether there is another combination of the level of the sensitivity of the communication receiver of the IMD that receives i2i communication signals from the other IMD, and the level of transmitter strength associated with the other IMD from which the IMD receives i2i communication signals, that will reduce a total system energy usage while satisfying the minimum acceptable SNR associated with the communication receiver; and wherein in response to determining that there is another combination that will reduce the total system energy usage while satisfying the minimum acceptable SNR, modifying the sensitivity of the communication receiver and/or transmitting an i2i communication signal to the other IMD that requests that the other IMD modify the transmitter strength associated with the other IMD, in order to implement the other combination and thereby reduce the total system energy usage while still satisfying the minimum acceptable SNR.

8. The method of claim 7, wherein the updating the strength metric based on the measured strength or the surrogate thereof comprises:

replacing a previous value of the strength metric with the measured strength or the surrogate thereof; or updating a moving average value of the strength metric using the measured strength or the surrogate thereof.

9. A method for use by an implantable medical device (IMD) that wirelessly communicates with another IMD, the method comprising:

receiving one or more implant-to-implant (i2i) communication signals from the other IMD using a communication receiver of the IMD;

measuring a strength of at least one of the one or more received i2i communication signals or a surrogate thereof;

updating a strength metric based on the measured strength or the surrogate thereof;

determining, based on the updated strength metric, whether to increase, decrease, or maintain a sensitivity of the communication receiver of the IMD; and selectively increasing, decreasing, or maintaining the sensitivity of the communication receiver of the IMD, based on a result of the determining, in a manner that respectively increases, decreases, or maintains an energy usage level of the communication receiver;

wherein the one or more i2i communication signals that the communication receiver of the IMD receives from the other IMD comprise both primary i2i communication signals and secondary i2i communication signals, the primary i2i communication signals for use in controlling delivery of therapy, and the secondary i2i communication signals for using in controlling the sensitivity of the communication receiver of the IMD; and wherein the measuring the strength of at least one of the one or more received i2i communication signals or the surrogate thereof, comprises measuring the strength of at least one of the secondary i2i communications signals.

10. The method of claim 9, wherein the updating the strength metric based on the measured strength or the surrogate thereof comprises:
    replacing a previous value of the strength metric with the measured strength or the surrogate thereof; or
    updating a moving average value of the strength metric using the measured strength or the surrogate thereof.

11. A method for use by an implantable medical device (IMD) that wirelessly communicates with another IMD, the method comprising:
    receiving one or more implant-to-implant (i2i) communication signals from the other IMD using a communication receiver of the IMD;
    measuring a strength of at least one of the one or more received i2i communication signals or a surrogate thereof;
    updating a strength metric based on the measured strength or the surrogate thereof;
    determining, based on the updated strength metric, whether to increase, decrease, or maintain a sensitivity of the communication receiver of the IMD; and
    selectively increasing, decreasing, or maintaining the sensitivity of the communication receiver of the IMD, based on a result of the determining, in a manner that respectively increases, decreases, or maintains an energy usage level of the communication receiver;
    wherein the measuring the strength of at least one of the one or more received i2i communication signals or the surrogate thereof, and the updating the strength metric, takes into account where within individual cardiac cycles different ones of the one or more i2i communication signals are received, and further comprising
    determining that an adjustment to when the other IMD transmits i2i communication signals within cardiac cycles enables the IMD to reduce the sensitivity and energy usage of the communication receiver of the IMD; and
    transmitting an i2i communication signal to the other IMD requesting that the other IMD adjust when the other IMD transmits i2i communication signals within individual cardiac cycles to thereby enable the IMD to reduce the sensitivity and energy usage of the communication receiver of the IMD.

12. The method of claim 11, wherein the updating the strength metric based on the measured strength or the surrogate thereof comprises:
    replacing a previous value of the strength metric with the measured strength or the surrogate thereof; or
    updating a moving average value of the strength metric using the measured strength or the surrogate thereof.

13. An implantable medical device (IMD) capable of wirelessly communicating with another IMD implanted within a patient, the IMD comprising:
    a communication receiver configured to receive implant-to-implant (i2i) communication signals from the other IMD, wherein a sensitivity of the communication receiver is adjustable within a sensitivity range that includes a minimum sensitivity setting and a maximum sensitivity setting;
    a communication transmitter configured to transmit i2i communication signals to the other IMD;
    a controller communicatively coupled to the communication receiver and the communication transmitter;
    measurement circuitry configured to measure a strength, or a surrogate thereof, of one or more i2i communication signals received by the communication receiver, the measurement circuitry part of the communication receiver and/or communicatively coupled to the controller; and
    a battery that powers the communication receiver, the measurement circuitry, and the controller;
    the controller configured to
        update a strength metric based on the measured strength or the surrogate thereof;
        compare the updated strength metric to one or more thresholds to make a determination as to whether the sensitivity of the communication receiver is to be increased, decreased or maintained;
        selectively increase, decrease, or maintain the sensitivity of the communication receiver of the IMD, based on a result of the comparison, in a manner that respectively increases, decreases, or maintains a level of energy that the communication receiver uses from the battery;
        cause the transmitter to transmit an i2i communication signal to the other IMD that requests that the other IMD increase a strength of one or more future i2i communication signals that will be transmitted by the other IMD to the IMD, when the communication receiver of the IMD is already at the maximum sensitivity setting and the determination is that the sensitivity of the communication receiver of the IMD is to be increased; and
        cause the transmitter to transmit an i2i communication signal to the other IMD that requests that the other IMD decrease a strength of one or more future i2i communication signals that will be transmitted by the other IMD to the IMD, when the communication receiver of the IMD is already at the minimum sensitivity setting and the determination is that the sensitivity of the communication receiver of the IMD is to be decreased.

14. The IMD of claim 13, wherein the controller is configured to update the strength metric based on the measured strength or the surrogate by:
    replacing a previous value of the strength metric with the measured strength or the surrogate thereof; or
    updating a moving average value of the strength metric using the measured strength or the surrogate thereof.

15. The IMD of claim 13, wherein:
    the communication receiver comprises an amplifier; and
    the controller is configured to selectively increase, decrease, or maintain the sensitivity of the communication receiver of the IMD by adjusting at least one of a gain, a bias current, or a switching frequency of the amplifier of the communication receiver.

16. An implantable medical device (IMD) capable of wirelessly communicating with another IMD implanted within a patient, the IMD comprising:
    a communication receiver configured to receive implant-to-implant (i2i) communication signals from the other IMD, wherein a sensitivity of the communication receiver is adjustable;
    a communication transmitter configured to transmit i2i communication signals to the other IMD;
    a controller communicatively coupled to the communication receiver and the communication transmitter;
    measurement circuitry configured to measure a strength, or a surrogate thereof, of one or more i2i communication signals received by the communication receiver, the measurement circuitry part of the communication receiver and/or communicatively coupled to the controller; and a battery that powers the communication receiver, the measurement circuitry, and the controller;

the controller configured to update a strength metric based on the measured strength or the surrogate thereof;

selectively increase, decrease, or maintain the sensitivity of the communication receiver of the IMD, based on the updated strength metric, in a manner that respectively increases, decreases, or maintains a level of energy that the communication receiver uses from the battery;

detect when it is likely that the other IMD transmitted an i2i communication signal that was not received by the communication receiver of the IMD; and cause the transmitter to transmit an i2i communication signal to the other IMD that requests that the other IMD increase the strength of one or more future i2i communication signals that will be transmitted by the other IMD to the IMD, in response to detecting that it is likely that the other IMD transmitted an i2i communication signal that was not received by the communication receiver of the IMD.

17. The IMD of claim 16, wherein the controller is configured to update the strength metric based on the measured strength or the surrogate by:

replacing a previous value of the strength metric with the measured strength or the surrogate thereof; or updating a moving average value of the strength metric using the measured strength or the surrogate thereof.

18. An implantable medical device (IMD) capable of wirelessly communicating with another IMD implanted within a patient, the IMD comprising:

a communication receiver configured to receive implant-to-implant (i2i) communication signals from the other IMD, wherein a sensitivity of the communication receiver is adjustable;

a communication transmitter configured to transmit i2i communication signals to the other IMD;

a sensor;

a controller communicatively coupled to the communication receiver, the communication transmitter, and the sensor;

measurement circuitry configured to measure a strength, or a surrogate thereof, of one or more i2i communication signals received by the communication receiver, the measurement circuitry part of the communication receiver and/or communicatively coupled to the controller; and a battery that powers the communication receiver, the measurement circuitry, and the controller;

the controller configured to update a strength metric based on the measured strength or the surrogate thereof;

selectively increase, decrease, or maintain the sensitivity of the communication receiver of the IMD based on comparisons between the updated strength metric and one or more thresholds;

use the sensor to monitor at least one of an activity level or a surrogate thereof of a patient within which the IMD is implanted; and adjust at least one of the one or more thresholds based on the activity level of the patient or the surrogate thereof that is monitored using the sensor.

19. The IMD of claim 18, wherein the controller is configured to update the strength metric based on the measured strength or the surrogate by:

replacing a previous value of the strength metric with the measured strength or the surrogate thereof; or updating a moving average value of the strength metric using the measured strength or the surrogate thereof.

20. The IMD of claim 18, wherein:

the communication receiver comprises an amplifier; and the controller is configured to selectively increase, decrease, or maintain the sensitivity of the communication receiver of the IMD by adjusting at least one of a gain, a bias current, or a switching frequency of the amplifier of the communication receiver.

* * * * *